United States Patent [19]
Richards et al.

[11] Patent Number: 6,153,741
[45] Date of Patent: Nov. 28, 2000

[54] DNA METHYLATION GENE FROM PLANTS

[75] Inventors: Eric J. Richards, St. Louis, Mo.;
Jeffrey A. Jeddeloh, New Market, Md.

[73] Assignee: Washington University, St. Louis, Mo.

[21] Appl. No.: 09/104,070

[22] Filed: Jun. 24, 1998

Related U.S. Application Data

[60] Provisional application No. 60/083,612, Apr. 30, 1998.

[51] Int. Cl.⁷ .............................. C12N 5/04; C12N 15/29; C12N 15/82; C12N 5/00; C07H 21/04
[52] U.S. Cl. ................. 536/23.6; 536/24.1; 435/69.1; 435/410; 435/411; 435/419; 800/278; 800/298; 800/306
[58] Field of Search ................................. 536/23.6, 24.1; 435/69.1, 410, 411, 419; 800/278, 298, 306

[56] References Cited

PUBLICATIONS

Boase et al. In Vitro Cellular and Developmental Biology. 1998. vol. 34: 46–51.
B.R. Cairns, Trends in Biochem. 23: 20–25, 1998.
Chen & Pikaard, Genes & Devel. 11: 2124–2136, 1997.
Jeddeloh et al., Genes Devel. 12:1714–1725, 1998.
Kakutani et al., Nuc. Acids Res. 23: 130–137, 1995.
Martinez–Balbas, M.A. et al., Proc. Natl. Acad. Sci. USA 95: 132–137, 1998.
Mittlesten Scheid et al., Proc. Natl. Acad. Sci. USA 95: 632–637, 1998.
Pazin, M.J. et al., Cell 88: 737–740, 1997.
Richards, Trends in Genetics 13: 319–323, 1998.

*Primary Examiner*—Lynette R. F. Smith
*Assistant Examiner*—Ousama M-Faiz Zaghmout
*Attorney, Agent, or Firm*—Janet E. Reed; Saul Ewing Remick & Saul, LLP

[57] ABSTRACT

A novel gene, DDM1, and its encoded protein are provided. The gene was isolated from a region of *Arabidopsis thaliana* chromosome 5. DDM1 appears to be part of the SWI2/SNF2 family of chromatin-remodeling proteins. Disruption of the gene results in DNA hypomethylation, among other phenotypes. The DDM1 gene defines a novel member of the DNA methylation system. Methods of using DDM1, and transgenic organisms comprising DDM1, are also provided.

10 Claims, 9 Drawing Sheets

DNA METHYLATION GENE FROM PLANTS

This application claims priority to U.S. Provisional Application Serial No. 60/083,612, filed Apr. 30, 1998, the entirety of which is incorporated by reference herein.

Pursuant to 35 U.S.C. §202(c), it is acknowledged that the U.S. Government has certain rights in the invention described herein, which was made in part with funds from the National Science Foundation.

FIELD OF THE INVENTION

This invention relates to the field of plant molecular biology, genetic engineering and regulation of gene expression. In particular, this invention provides a novel gene, DDM1, which plays an important role in the regulation of DNA methylation, and resultant regulation of gene expression, in plant genomic DNA.

BACKGROUND OF THE INVENTION

Plant genomes contain substantial amounts of 5-methylcytosine. Up to 20–30% of the cytosines are methylated in the nuclear genome of many flowering plants. As in other organisms, methylation of cytosine residues in plants occurs post-replicatively through the action of cytosine-DNA methyltransferases. Plant DNA methyltransferases have been characterized biochemically, and plant genes encoding these enzymes have been isolated by virtue of their similarity to their mammalian counterparts.

Investigations of native plant genes and transgenic plants containing foreign genes have found a general correlation between transcriptional inactivity and increased DNA methylation, consistent with evidence from mammalian systems. This evidence supports a role for cytosine methylation in maintaining transcriptional states.

The plant's need for developmental plasticity and environmental interaction suggests that plants extensively employ epigenetic regulatory strategies. Such strategies rely on heritable, often reversible, changes in access to the underlying genetic information, but not alteration of the primary nucleotide sequence. As one example, the alteration of DNA methylation is expected to perturb plant development significantly, provided that differential DNA methylation is an important component of epigenetic regulation in plants.

One paradigm linking DNA methylation and developmental regulation comes from work on the mouse, where average genome cytosine methylation levels in embryonic lineages drop sharply in the early cleavages following fertilization, then rise again around the time of implantation. In plants, a similar pattern has been observed in studies of DNA methylation content in pollen and post-embryonic tissue of varying age. Information from such studies indicates that there is a gradual rise in 5-methylcytosine levels in post-embryonic tissues produced by meristems at positions further from the base of the plant (i.e., tissues of increasing age). Genetic studies of transposon systems in maize also demonstrate an age-dependent gradient of increasing epigenetic modification, which is correlated with DNA methylation.

Both biochemical and genetic approaches have been taken to alter DNA methylation in eucaryotic organisms. Methylation inhibitor treatments have induced developmental abnormalities in many plant species. Transgenic plants expressing antisense molecules specific for a native cytosine methyltransferase gene have been found to exhibit genomic hypomethylation, presumably due to the antisense interference with expression of the gene.

In another approach, mutants of *Arabidopsis thaliana* have been isolated, which show a decrease in DNA methylation (ddm) resulting in reduced nuclear 5-methylcytosine levels. The best characterized mutations define the DDM1 gene. Homozygotes carrying recessive ddm1 alleles contain 30% of the wild-type levels of 5-methylcytosine. The ddm1 mutations do not map to the two known cytosine-DNA methyltransferase genes of *A. thaliana*, nor do they affect DNA methyltransferase activity detectable in nuclear extracts (Kakutani et al., Nuc. Acids Res. 23: 130–137, 1995). In addition, ddm1 mutations do not appear to affect the metabolism of the active methyl group donor, S-adenosylmethionine (Kakutani et al., 1995, supra).

For the foregoing reasons, the DDM1 gene product is likely to be a novel component of the DNA methylation system, or involved in determining the cellular context (e.g., chromatin structure, subnuclear localization) of the methylation reaction. Consequently, it would be a clear advance in the art of plant molecular and cellular biology to identify and isolate the DDM1 gene and/or its encoded protein. Such a gene and protein would find utility for the purpose of modifying the methylation status of a selected genome and thereby altering one or more regulatory features of gene expression from that genome.

SUMMARY OF THE INVENTION

A novel gene, DDM1, and its encoded protein are provided in accordance with the present invention. The gene has been identified as a novel element of the DNA methylation system.

In one aspect of the invention, an isolated nucleic acid molecule comprising a gene located on *Arabidopsis thaliana* chromosome 5, lower arm, is provided. The gene occupies a segment of chromosome 5, lower arm, which is flanked on the centromeric side within 20 kilobases by a gene encoding a zinc-finger protein and on the telomeric side within 1 kilobase by a gene encoding a glutamic acid tRNA. Disruption of the gene is associated with DNA hypomethylation. The gene encodes a polypeptide of about 800 amino acids in length. The nucleotide sequence of the DDM1 gene is set forth herein as SEQ ID NO:1 and its deduced amino acid sequence as SEQ ID NO:2.

In another aspect of the invention, an isolated DDM1 gene is provided, having a sequence selected from the group consisting of: (a) Sequence I.D. No. 1; (b) an allelic variant or natural mutant of Sequence I.D. No. 1; (c) a sequence hybridizing with part or all of Sequence I.D. No. 1 or its complement and encoding a polypeptide substantially the same as part or all of a polypeptide encoded by Sequence I.D. No. 1; (d) a sequence encoding part or all of a polypeptide having amino acid Sequence I.D. No. 2; and (e) a sequence encoding part or all of a polypeptide contained in the cosmid clone C38, designated ATCC Accession No. 207208.

According to another aspect of the invention, a polypeptide is provided, which is produced by expression of an isolated nucleic acid molecule comprising part or all of an open reading frame of a gene located on *Arabidopsis thaliana* chromosome 5, lower arm, the gene occupying a segment of chromosome 5, lower arm, flanked on the centromeric side within 20 kilobases by a gene encoding a zinc-finger protein and on the telomeric side within 1 kilobase by a gene encoding a glutamic acid tRNA. This polypeptide preferably has the amino acid sequence of part or all of Sequence I.D. No. 2.

According to another aspect of the invention, an isolated protein encoded by an *Arabidopsis thaliana* gene is provided, which is a member of an SWI2/SNF2 family of polypeptides. Loss of function of the protein is associated with DNA hypomethylation. The protein is encoded by a gene located on A. thaliana chromosome 5, lower arm, centromerically flanked within 20 kilobases by a zinc finger-encoding gene and telomerically within one kilobase by a gene encoding a glutamic acid tRNA.

According to another aspect of the invention, a transgenic organism comprising the DDM1 gene is provided. In one embodiment, the transgenic organism is a plant.

In other aspects of the invention, methods are provided for stabilizing fidelity of DNA methylation in an organism, which comprise transforming the organism with the DDM1 gene. Methods are also provided for reducing or eliminating gene silencing in a plant, or for inducing inbreeding depression in a plant, which comprise inhibiting or preventing expression of an endogenous DDM1 gene of the plant.

These aspects of the invention, as well as other features and advantages of the invention, will be described in greater detail in the description and examples set forth below.

BRIEF DESCRIPTION OF THE DRAWINGS

FIG. 7. DDM1 gene identification.

DETAILED DESCRIPTION OF THE INVENTION

I. Definitions

Figure 1:
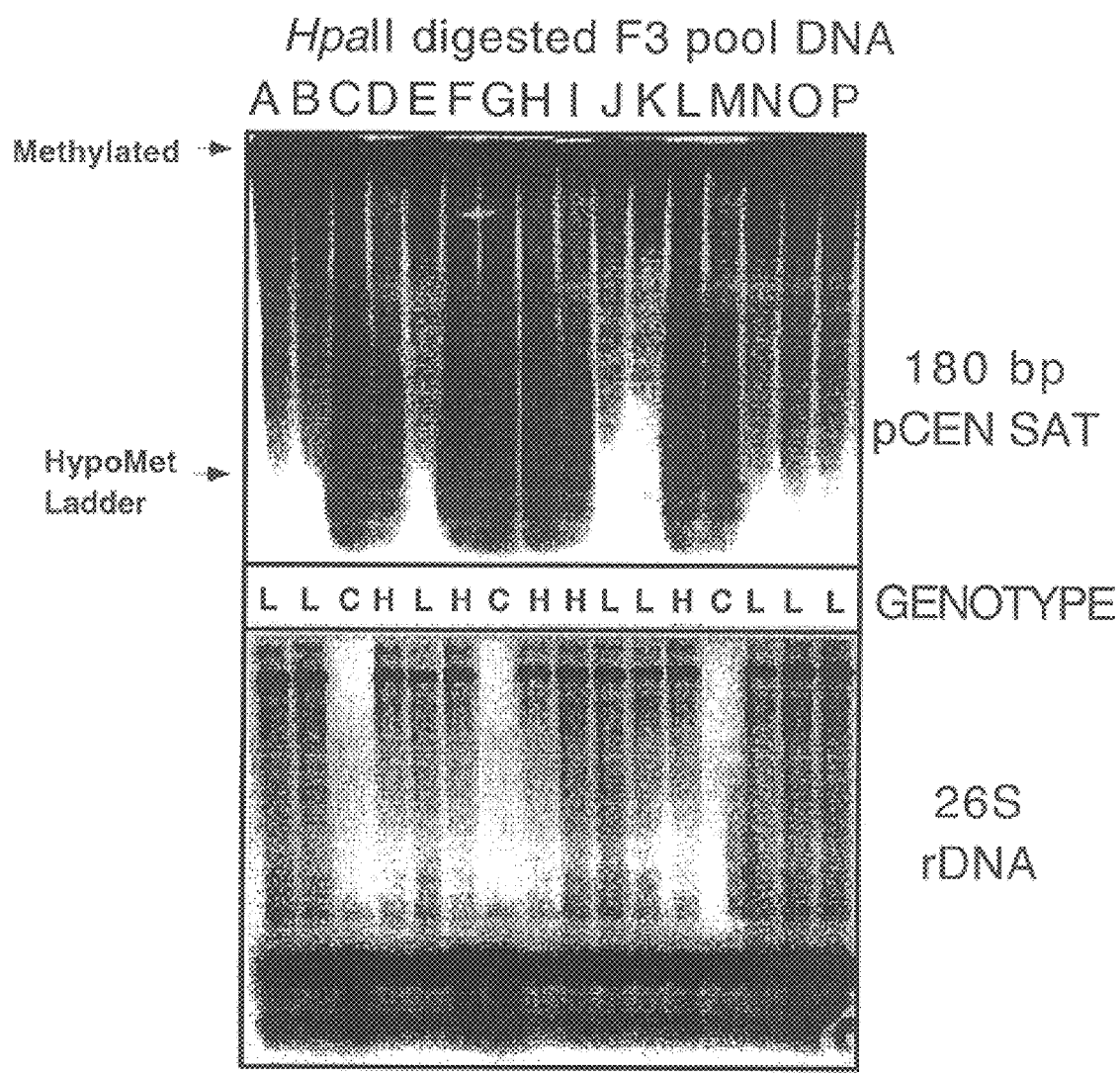
FIG. 1. Autoradiograph showing Southern analysis of F3 recombinant pools in a ddm1 segregating family genotyping. HpaI-digested DNA from different families (pools A–P) was electrophoresed on a 1% agarose gel, then blotted to a nylon filter. Each pool represents about 20–30 individuals from each family. The families were genotyped by comparing the results with the pericentric 180 pb probe (+ladder= hypomethylated: ddm1/DDM1 or ddm1/ddm1;–ladder= DDM1/DDM1) to the 26S rDNA probe (loss of large fragment=ddm1/ddm1) (L=homozygous for the Landsberg allele; C=homozygous for the Columbia allele; H=heterozygous).

Various terms relating to the biological molecules of the present invention are used hereinabove and also throughout the specification and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention.

Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers to the 5' regulatory regions of a gene.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants and generate progeny transgenic plants. These constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

II. Description of DDM1 and its Encoded Polyeptide

In accordance with the present invention, a novel gene, DDM1, has been isolated from the flowering plant *Arabidopsis thaliana*. Through analysis of mutant plants, this gene has been identified as important for the maintenance of proper genomic cytosine methylation, and its function appears to be necessary to maintain gene silencing. Biochemical and molecular genetic results indicate that DDM1 encodes a novel component of the DNA methylation machinery.

Figure 8:
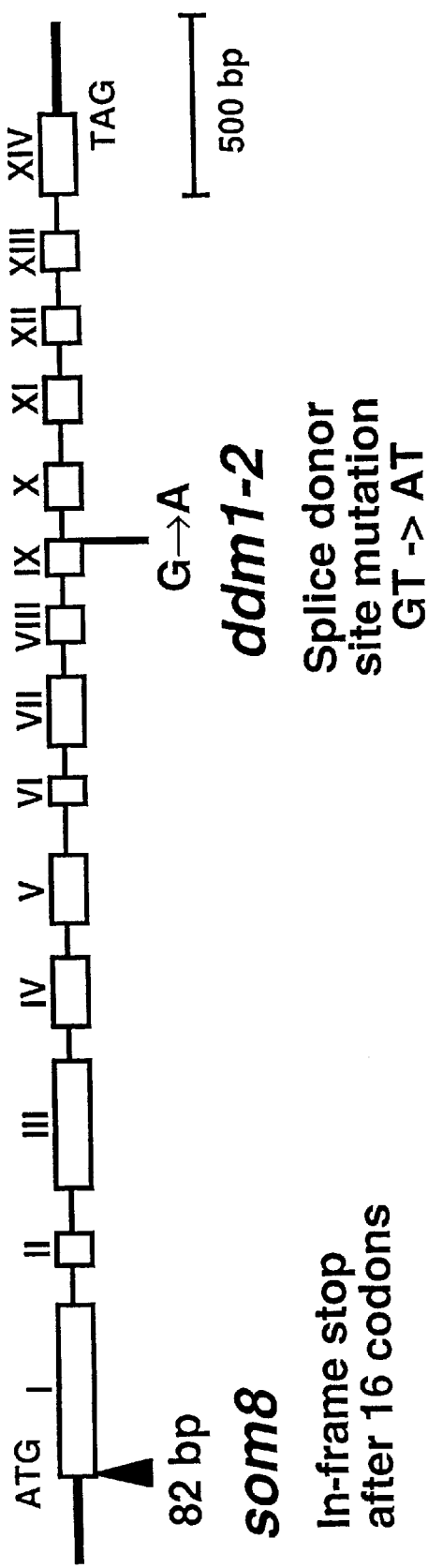
FIG. 8. Diagram showing DDM1 gene structure. The exon-intron structure of the DDM1 gene is shown, as well as the positions of the two molecularly characterized ddm1 alleles (som8 & ddm1-2).
Figure 9:
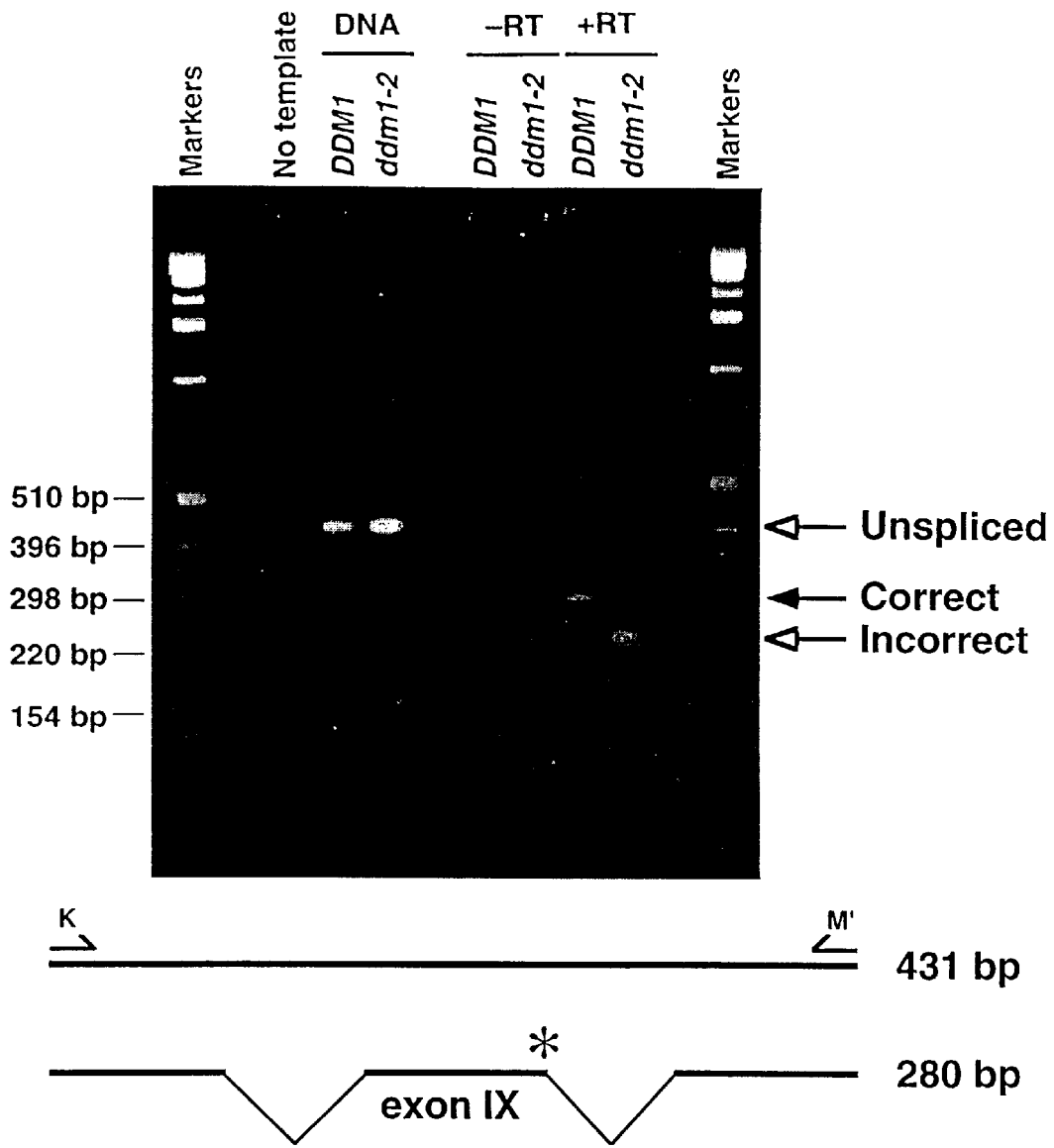
FIG. 9. RT-PCR detection of DDM1 expression and the ddm1-2 splicing defect—ethidium bromide stained size-fractionated products of PCR amplification using various templates. The nature of the templates is indicated at the top of the gel: DNA=genomic DNA from either DDM1 or ddm1-2 plants; –RT=mock cDNA synthesized template carried out in the absence of reverse transcriptase; +RT=first strand cDNA synthesis carried out on polyA+RNA purified from either DDM1 or ddm1-2 plants. The predicted size of the amplification products is shown at the bottom of the figure. K and M' were used as oligonucleotide primers for PCR amplification. The RT-PCR product from ddm1-2 cDNA templates shows an altered mobility indicative of a splicing defect.

We have isolated the DDM1 gene from *A. thaliana* using a map-based cloning approach, which is described in detail in the examples. Briefly, the DDM1 gene was initially localized to the bottom of the lower arm of chromosome 5 by reference to molecular markers segregating in an F2 family (parental cross: Columbia ddm1/ddm1 X Landsberg erecta DDM1/DDM1). Next, recombination breakpoints in the region surrounding a ddm1 mutation were isolated by collecting cross-over chromosomes by reference to flanking genetic markers. The recombination breakpoints delimited a region of approximately 25 kilobases. Cloned DNA corresponding to this genomic region was isolated by subcloning DNA from a bacterial artificial chromosome (BAC) containing molecular markers mapping both proximal and distal to the ddm1 marker. The nucleotide sequence of a single cosmid subclone encompassing the 25 kb region was determined to identify candidate genes. The DDM1 gene was localized to one of the seven predicted protein-coding genes in the region by reference to DNA polymorphisms. A well-characterized EMS-induced mutation, ddm1-2, leads to a conformational polymorphism in a RsaI restriction fragment in the 3' end of the gene. The ddm1-2 mutation is a base pair substitution (G→A) in a splice site donor site leading to an alteration in mRNA structure (FIGS. 8 and 9). Moreover, a putative ddm1 allele, som8, carries a structural rearrangement at the predicted 5' end of the gene. Subsequent DNA sequence analysis indicated that the som8 mutation is a complex rearrangement (83 bp insertion plus a 1 bp deletion) directly following the predicted translation start site. The som8 mutation destroys the open reading frame of the first protein-coding exon and leads to premature termination after only 16 codons (FIG. 8). The affected gene encodes a SWI2/SNF2-like protein product with a large degree of amino acid similarity to yeast, Drosophila and mammalian SWI2/SNF2-like products.

The prototype SWI2/SNF2 gene was identified in yeast as a non-lethal gene necessary to effect expression of mating type and sucrose metabolism genes. Subsequently, a number of related genes, some of which are essential for growth, have been identified in yeast, Drosophila and mammals. The proteins encoded by the SWI2/SNF2 gene family act as a part of large, multi-subunit complexes that remodel chromatin (Pazin, M. J. et al., Cell 88: 737–740, 1997). In most cases, these complexes act as transcriptional activators by providing transcription factor access to the DNA sequences packaged in the nucleosomes.

Without intending to be bound by any particular mechanism for the functionality of the DDM1 gene product, we believe the DDM1 SWI2/SNF2-like gene may encode a component of a remodeling complex that is specialized to facilitate maintenance methyltransferase access to newly-replicated DNA packaged in chromatin. This model provides an explanation for the ddm1 mutations' preferential hypomethylation of highly repeated sequences, which are expected to be more tightly packed than single-copy sequences.

We anticipate a number of applications for our novel gene and its encoded protein, and our discovery of the involvement of a SWI2/SNF2-like gene in the eucaryotic DNA methylation system. Such applications are described in greater detail below.

Although the DDM1 genomic clone from *Arabidopsis thaliana* is described and exemplified herein, this invention is intended to encompass nucleic acid sequences and proteins from other organisms, including plants, yeast, insects and mammals, that are sufficiently similar to be used instead of the Arabidopsis DDM1 nucleic acid and proteins for the purposes described below. These include, but are not limited to, allelic variants and natural mutants of Sequence I.D. No. 1, which are likely to be found in different species of plants or varieties of Arabidopsis. Because such variants are expected to possess certain differences in nucleotide and amino acid sequence, this invention provides an isolated DDM1 nucleic acid molecule having at least about 60% (preferably 70% and more preferably over 80%) sequence homology in the coding regions with the nucleotide sequence set forth as Sequence I.D. No. 1 (and, most preferably, specifically comprising the coding region of sequence I.D. No. 1). This invention also provides isolated polypeptide products of the open reading frames of Sequence I.D. No. 1, having at least about 60% (preferably 70% or 80% or greater) sequence homology with the amino acid sequences of Sequence I.D. No. 2. Because of the natural sequence variation likely to exist among DDM1 genes, one skilled in the art would expect to find up to about 30–40% nucleotide sequence variation, while still maintaining the unique properties of the DDM1 gene and encoded polypeptide of the present invention. Such an expectation is due in part to the degeneracy of the genetic code, as well as to the known evolutionary success of conservative amino acid sequence variations, which do not appreciably alter the nature of the encoded protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. its structure and/or biological activity). With particular reference to nucleic acid sequences, the term "substantially the same" is intended to refer to coding regions and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide that do not affect structure or function. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1997) (hereinafter "Ausubel et al.") are used.

A. Preparation of DDM1 Nucleic Acid Molecules, Encoded Polypeptides and Antibodies Specific for the Polypeptides 1. Nucleic Acid Molecules DDM1 nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

DDM1 genes also may be isolated from appropriate biological sources using methods known in the art. In the exemplary embodiment of the invention, the *A. thaliana* DDM1 clone was isolated from a BAC genomic library of *A. thaliana* In alternative embodiments, cDNA clones of DDM1 may be isolated. A preferred means for isolating DDM1 genes is PCR amplification using genomic templates and DDM1-specific primers.

In accordance with the present invention, nucleic acids having the appropriate level sequence homology with part or all the coding regions of Sequence I.D. No. 1 may be identified by using hybridization and washing conditions of appropriate stringency. For example, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 2×SSC and 0.1% SDS; (4) 2 hours at 45–55° in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$T_m = 81.5° C. + 16.6 Log [Na+] + 0.41(\% G+C) - 0.63 (\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the sequences of the present invention.

Nucleic acids of the present invention may be maintained as DNA in any convenient cloning vector. In a preferred embodiment, clones are maintained in plasmid cloning/ expression vector, such as pGEM-T (Promega Biotech, Madison, Wis.) or pBluescript (Stratagene, La Jolla, Calif.), either of which is propagated in a suitable *E. coli* host cell.

DDM1 nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the DNA having Sequence I.D. No. 1. Such oligonucleotides are useful as probes for detecting DDM1 genes or mRNA in test samples, e.g. by PCR amplification, or for the positive or negative regulation of expression of DDM1 genes at or before translation of the mRNA into proteins.

The DDM1 promoter and other expression regulatory sequences for DDM1 are also expected to be useful in connection with the present invention. Sequence I.D. No. 1 shows about 750 bp of sequence upstream from the beginning of the coding region, which should contain such expression regulatory sequences. In addition, Sequence I.D. No. 3 (see the Example) constitutes about 5 kbp of additional upstream sequence, which may contain other regulatory sequences, such as enhancer elements.

2. Proteins

Polypeptides encoded by DDM1 nucleic acids of the invention may be prepared in a variety of ways, according to known methods. If produced in situ the polypeptides may be purified from appropriate sources, e.g., plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of DDM1-encoded polypeptide may be produced by expression in a suitable procaryotic or eucaryotic system. For example, part or all of a DNA molecule, such as the coding portion of Sequence I.D. No. 1, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The DDM1 polypeptide produced by gene expression in a recombinant procaryotic or eucyarotic system may be purified according to methods known in the art. In a preferred embodiment, a commercially available expression/ secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The DDM1-encoded polypeptides of the invention, prepared by the aforementioned methods, may be analyzed according to standard procedures. Methods for analyzing the functional activity are available. For instance, DNA methylation levels are detectable by known methods. Alternatively, the function of the DDM1 gene product as part of a chromatin remodeling machine permits the use of in vitro assays for chromatin remodeling, which are known in the art (e.g., B. R. Cairns, Trends in Biochem. 23: 20–25, 1998).

The present invention also provides antibodies capable of immunospecifically binding to polypeptides of the invention. Polyclonal or monoclonal antibodies directed toward the polypeptide encoded by DDM1 may be prepared according to standard methods. Monoclonal antibodies may be prepared according to general methods of Köhler and Milstein, following standard protocols. In a preferred embodiment, antibodies are prepared, which react immunospecifically with various epitopes of the DDM1-encoded polypeptides.

B. Uses of DDM1 Nucleic Acids, Encoded Proteins and Antibodies

1. DDM1 Nucleic Acids

DDM1 nucleic acids may be used for a variety of purposes in accordance with the present invention. The DNA, RNA, or fragments thereof may be used as probes to detect the presence of and/or expression of DDM1 genes. Methods in which DDM1 nucleic acids may be utilized as probes for such assays include, but are not limited to: (1) in situ hybridization; (2) Southern hybridization (3) northern hybridization; and (4) assorted amplification reactions such as polymerase chain reactions (PCR).

The DDM1 nucleic acids of the invention may also be utilized as probes to identify related genes from other species, including but not limited to, plants, yeast, insects and mammals, including humans. As is well known in the art and described above, hybridization stringencies may be adjusted to allow hybridization of nucleic acid probes with complementary sequences of varying degrees of homology. Thus, DDM1 nucleic acids may be used to advantage to identify and characterize other genes of varying degrees of relation to the exemplary coding sequence of Sequence I.D. No. 1, thereby enabling further characterization of this family of genes. Additionally, they may be used to identify genes encoding proteins that interact with protein encoded by DDM1 (e.g., by the "interaction trap" technique).

As discussed above and in greater detail in Example 1, the similarity among plant DDM1 and its SWI2/SNF2 counterparts in yeast, Drosophila and mammals indicates that the functional aspects of these proteins will also be conserved. Thus, DDM1 is expected to play an important role in DNA methylation and resultant down-regulation of gene expression. Plants engineered to over-express DDM1 can be expected to have improved fidelity of the DNA methylation system. The evidence suggests that loss of DDM1 function leads to reduction in the efficiency of maintenance methylation due to reduced accessibility of the methyltransferase enzyme to the substrate. Hence, excess DDM1 function could lead to an increase in the fidelity of the inheritance of DNA methylation thereby reducing the occurrence of spurious methylation mistakes which could compromise the organism's viability or fecundity. In fact, there are experimental data demonstrating that loss of DDM1 function leads to stochastic hypermethylation, and epigenetic lesion formation, as well. For these reasons, DDM1 overexpression lines are expected to have useful properties.

Transgenic plants expressing the DDM1 gene or antisense nucleotides can be generated using standard plant transformation methods known to those skilled in the art. These include, but are not limited to, Agrobacterium vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The method of transformation depends upon the plant to be transformed. The biolistic DNA delivery method is useful for nuclear transformation. In another embodiment of the invention, Agrobacterium vectors are used to advantage for efficient transformation of plant nuclei.

In a preferred embodiment, the gene is introduced into plant nuclei in Agrobacterium binary vectors. Such vectors include, but are not limited to, BIN19 (Bevan, 1984) and derivatives thereof, the pBI vector series (Jefferson et al., 1987), and binary vectors pGA482 and pGA492 (An, 1986).

The DDM1 gene may be placed under a powerful constitutive promoter, such as the Cauliflower Mosaic Virus (CaMV) 35S promoter or the figwort mosaic virus 35S promoter. Transgenic plants expressing the DDM1 gene under an inducible promoter (either its own promoter or a heterologous promoter) are also contemplated to be within the scope of the present invention. Inducible plant promoters include the tetracycline repressor/operator controlled promoter.

Using an Agrobacterium binary vector system for transformation, the DDM1 coding region, under control of a constitutive or inducible promoter as described above, is linked to a nuclear drug resistance marker, such as kanamycin resistance. Agrobacterium-mediated transformation of plant nuclei is accomplished according to the following procedure:

(1) the gene is inserted into the selected Agrobacterium binary vector;

(2) transformation is accomplished by co-cultivation of plant tissue (e.g., leaf discs) with a suspension of recombinant Agrobacterium, followed by incubation (e.g., two days) on growth medium in the absence of the drug used as the selective medium (see, e.g., Horsch et al. 1985);

(3) plant tissue is then transferred onto the selective medium to identify transformed tissue; and (4) identified transformants are regenerated to intact plants.

It should be recognized that the amount of expression, as well as the tissue specificity of expression of the DDM1 gene in transformed plants can vary depending on the position of their insertion into the nuclear genome. Such position effects are well known in the art. For this reason, several nuclear transformants should be regenerated and tested for expression of the transgene.

In some instances, it may be desirable to down-regulate or inhibit expression of endogenous DDM1 in plants possessing the gene. One clear benefit to engineering a reduction of DDM1 function is to reduce gene (including transgene) silencing. Plant lines with reduced or absent DDM1 function are expected to be viable based on results obtained with Arabidopsis. Further, it has been shown that gene silencing is suppressed in ddm1 Arabidopsis lines (Jeddeloh et al., Genes Devel. 12:1714–1725, 1998). There are two other beneficial characteristics of DDM1 deficient plant lines. First, alteration in DNA methylation leads to changes in flowering time, and as such, is a potentially powerful tool for manipulating plant development. (See, e.g., Richards, Trends in Genetics 13: 319–323, 1998), Second, ddm1 mutant lines exhibit inbreeding depression (a reduction in vigor after inbreeding) (Richards, Trends in Genetics, 1998, supra), a characteristic which may be desirable to include in situations where proprietary germplasms in hybrid plants are at risk of unauthorized use. For instance, a genetically engineered hybrid (containing one or more useful transgenes) could be further engineered to down-regulate endogenous DDM1 expression. Unauthorized inbreeding of such lines would be discouraged because the progeny of such lines would lack vigor.

To achieve the aforementioned benefits associated with reduced gene expression, DDM1 nucleic acid molecules, or fragments thereof, may also be utilized to control the production of DDM1-encoded proteins. In one embodiment, full-length DDM1 antisense molecules or antisense oligonucleotides, targeted to specific regions of DDM1-encoded RNA that are critical for translation, are used. The use of antisense molecules to decrease expression levels of a predetermined gene is known in the art. In a preferred embodiment, antisense molecules are provided in situ by transforming plant cells with a DNA construct which, upon transcription, produces the antisense sequences. Such constructs can be designed to produce full-length or partial antisense sequences.

In another embodiment, overexpression of DDM1 is induced to generate a co-suppression effect. This excess expression serves to promote down-regulation of both endogenous and exogenous DDM1 genes.

Optionally, transgenic plants can be created containing mutations in the region encoding the active site of DDM1. This embodiment may be preferred in certain instances.

From the foregoing discussion, it can be seen that DDM1 and its homologs will be useful for introducing alterations in gene expression in an organism, for a variety of purposes. As described above, for instance, the Arabidopsis DDM1 gene can be used to isolate mutants or engineer organisms that express reduced function of DDM1 orthologs. Based on results in Arabidopsis, such mutants or engineered organisms are expected to be viable and display valuable characteristics, such as inbreeding depression and a reduction in gene silencing. In addition, we anticipate that dysfunction in human DDM1 orthologs may contribute to diseases that involve alterations in DNA methylation, including cancer (Baylin, S. B. et al., Adv. Cancer Res. 72: 141–196, 1998) and immunodeficiency/chromosome instability/facial anomalies syndrome (ICF) (Smeets, D. F. C. M. et al., Hum. Genet. 94: 240–246, 1994).

2. DDM1 Proteins and Antibodies

Purified DDM1-encoded proteins, or fragments thereof, may be used to produce polyclonal or monoclonal antibodies which also may serve as sensitive detection reagents for the presence and accumulation of DDM1-encoded protein in cultured cells or tissues and in intact organisms. Recombinant techniques enable expression of fusion proteins containing part or all of the DDM1-encoded protein. The full length protein or fragments of the protein may be used to advantage to generate an array of monoclonal or polyclonal antibodies specific for various epitopes of the protein, thereby providing even greater sensitivity for detection of the protein in cells or tissue.

DDM1 gene products also may be useful as pharmaceutical agents if it is determined that DDM1 loss of function plays a role in carcinogenesis, as mentioned above. The gene products could be administered as replacement therapy for persons having neoplasias associated with DDM1 loss of function.

Polyclonal or monoclonal antibodies immunologically specific for DDM1-encoded proteins may be used in a variety of assays designed to detect and quantitate the protein. Such assays include, but are not limited to: (1) flow cytometric analysis; (2) immunochemical localization in cultured cells or tissues; and (3) immunoblot analysis (e.g., dot blot, Western blot) of extracts from various cells and tissues.

Polyclonal or monoclonal antibodies that immunospecifically interact with the polypeptide encoded by DDM1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

The following specific example is provided to illustrate embodiments of the invention. It is not intended to limit the scope of the invention in any way.

EXAMPLE

Molecular Isolation of the DDM1 Locus From
Arabidopsis thaliana

DDM1 is likely to be a novel component of the DNA methylation machinery because the known components had been eliminated by genetic and biochemical analysis. We decided that positionally isolating the DDM1 locus would provide insight as to the mode of ddm1-induced hypomethylation. Crude mapping experiments had positioned the ddm1 locus on the south arm of A. thaliana chromosome five. Based upon our map position and the relative genetic distance to some known genetic markers for which there existed a genotype in our segregating families, we believed that the ddm1 lesions should lie between the mutations known as yi (yellow inflorescence) and aba (abscisic acid deficient) (see FIG. 2). Generation of recombinant chromosomes would be necessary for the positional cloning strategy.

Figure 2:
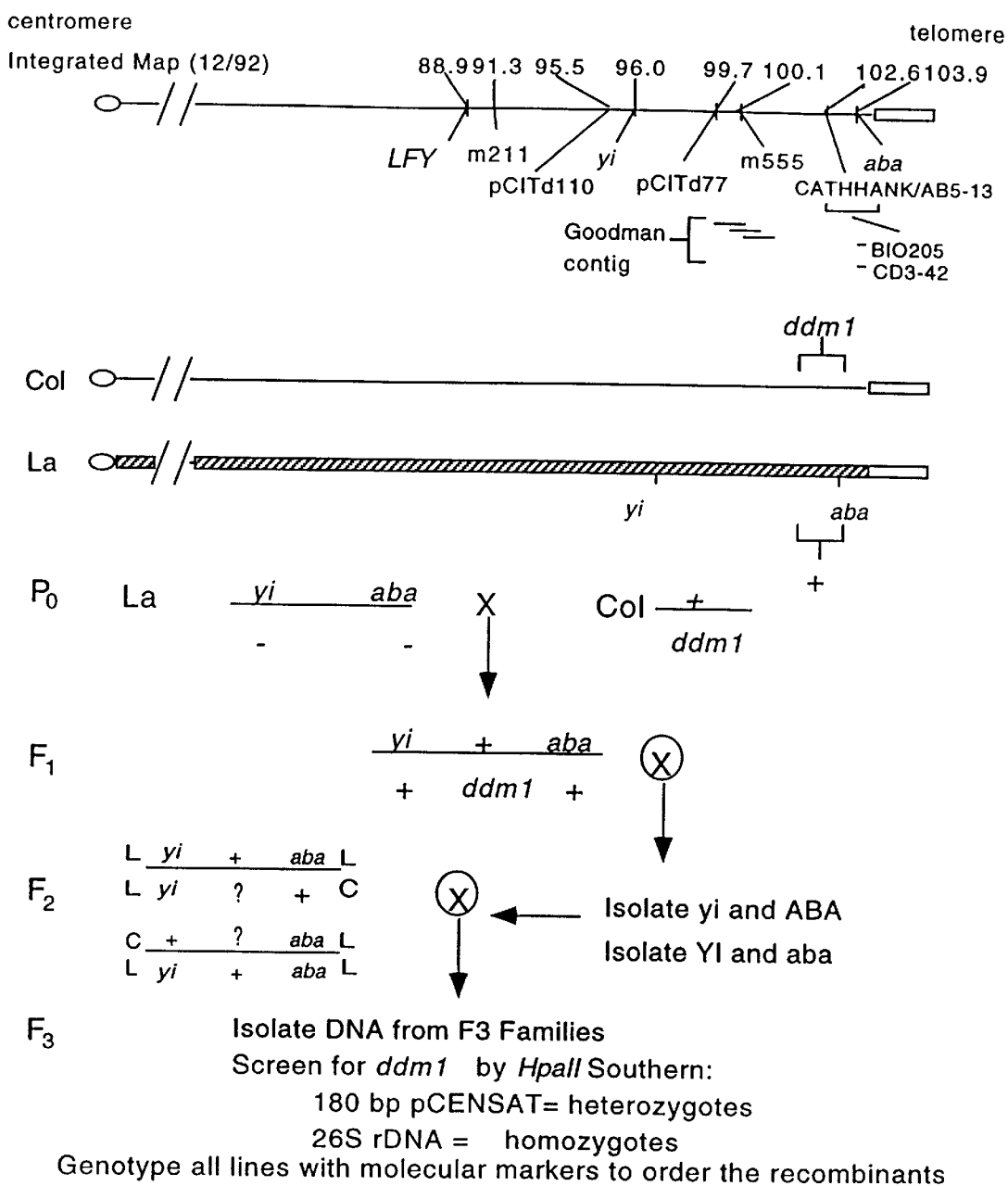
FIG. 2. Diagram and summary showing scheme for positional cloning of DDM1 locus on Arabidopsis thaliana chromosome 5.

COLLECTION OF RECOMBINATION
BREAKPOINTS AROUND DDM1:

Our strategy is outlined in FIG. 2. Our ddm1 mutations were isolated in the Columbia strain background and backcrossed to this parent six times, and then selfed to generate a segregating ddm1 family. We chose the Landsberg strain to cross against allowing us to follow parental origin of any region of the genome. The Landsberg yi aba line was kindly provided by Dr. Jan Zeevart, Michigan State University.

We first crossed a YI ddm1 ABAI YI DDM1 ABA line in the Columbia background to a Landsberg yi DDM1 aba/yi DDM1 aba line. One half of the F1 would be the desired genotype YI ddm1 ABA/yi DDM1 aba. These F1 were identified by progeny testing-scoring for plants which segregated ddm1 hypomethylated DNA. These ddm1/DDM1 F1 plants contain hypomethylated pericentric DNA in their silique tissue that can be detected in these pools by Southern analysis, as in the original screen for isolating the mutants.

Figure 3:
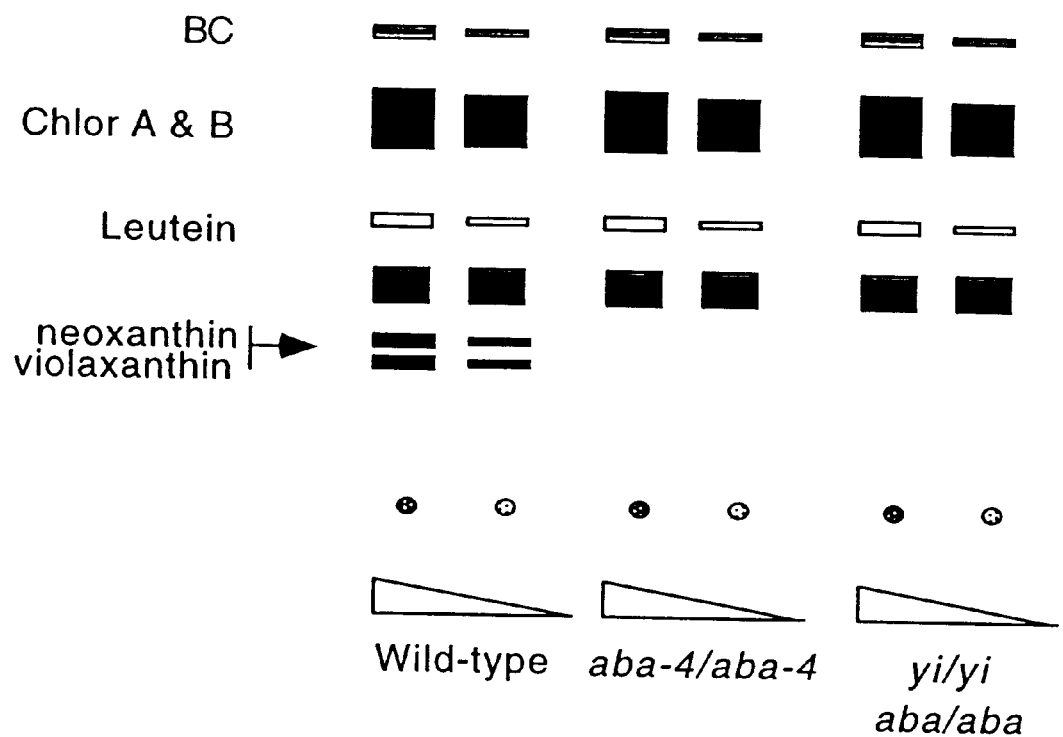
FIG. 3. Schematic diagram of thin-layer chromatography analysis of carotenoid extracts from A. thaliana wild-type and aba mutant tissues. BC indicates the position of beta-carotene. Chlor A & B indicates the smear of chlorophyll A and B. The smear below leutein is Chlorophyll A and B stripped of magnesium ions. Notice the aba plants fail to accumulate neoxanthin and violaxanthin, and that yi has no effect on the pattern.

Selfed seed from F1 YI ddm1 ABA/yi DDM aba were collected dried and then sown. Individuals that possess a recombination breakpoint in the yi aba interval were recovered by screening the F2 progeny for the following visible phenotypes: yi ABA and YI aba. yi plants are detected ~1 wk post germination by the presence of a yellow inflorescence. aba mutant individuals were identified by two methods. First, a wilting test was done by shifting the plants from the 85% relative humidity in the growth chamber to the dry lab air. aba plants cannot correctly control the turgor pressure of their stomatal guard cells and rapidly wilt. This screen was prone to mis-identifying aba mutants so a secondary screen was also used. The secondary verification of the aba mutant phenotype was done by thin layer chromatography (TLC) (FIG. 3). The phytohormone abscisic acid (ABA) is produced as a final byproduct of carotenoid biosynthesis. aba mutants are blocked before aba can be produced. As a result they fail to produce two carotenoids, neoxanthin and violaxanthin. aba mutants lack two blue bands just above the origin (corresponding to the carotenoids neoxanthin and violaxanthin). 135 F2 plants were recovered that were either yi ABA or YI aba. The predicted genetic distance between yi and aba was determined to be ~8 cM (integrated map 5/92), which meant that recombinants were expected to be recovered at about a frequency of ~10%.

It was critical to use a ddm1/+ plant rather than a ddm1/ddm1 plant in this cross because ddm1 hypomethylated DNA is not remethylated in a wt background (Vongs et al., science 260: 1926–1928, 1993). Because the hypomethylated chromosomes are not remethylated in a DDM1 nucleus, hypomethylated chromosome segments will each segregate as a Mendelian locus. Since we use the methylation status of the rDNA and centromere to score the genotype at ddm1, segregation of hypomethylated chromosome segments in addition to the ddm1 mutation could result in the mis-genotyping of a potential recombination event. The entire problem was avoided by using a heterozygous parent as the donor for the ddm1 mutation, because the mutation is fully recessive, no hypomethylated DNA was introduced into the cross and no miss-genotyping could occur later.

DNA was prepared from 111 of the 135 recombinant lines by growing F3 progeny tissue. The F3 DNA samples were scored for the DNA hypomethylation phenotype diagnostic of ddm1. HpaII digests were done and two Southern blots were performed. First, the centromeric (180 bp) repeat probe was used to identify lines which were either heterozygous or homozygous for ddm1 in the F2 generation. Second, we used a 26S rDNA probe (FIG. 1). Only F2 plants homozygous for the ddm1 mutation would show complete hypomethylation with the 26S probe. Therefore lines homozygous for ddm1 should show a ladder with the centromeric probe and complete hypomethylation with the rDNA probe. Lines heterozygous for ddm1 show hypomethylation only with the centromeric probe, and lines wild-type for DDM1 show no ladders at all. In the 111 lines, 84 recombination events occurred between YI and ddm1 and 36 events occurred between ddm1 and ABA. This placed ddm1 in the YI ABA interval and closer to ABA than YI.

Once all of the lines were scored for ddm1, the lines were scored for two available molecular markers predicted to be in the interval, CATHHANK and BIO205. Of the 87 lines scored for all three internal markers 17 lines were recombinant between CATHHANK and ddm1, and 9 lines were recombinant between ddm1 and BIO205. The interval between CATHHANK and BIO205 was predicted to be 2.6 cM (Recombinant Inbred map 6/95 (http://nasc.nott.ac.uk)). With 28 recombination events in 2.6 cM we had 1 crossover per 0.09 cM. In Arabidopsis the average number of Kb per cM is 200, suggesting that we had an average of one crossover every 19 Kb through the interval. At this stage we stopped collecting recombinants and focused on refining the interval by placing new and recently developed markers onto the genetic map. At the same time we utilized the available flanking molecular markers (CATHHANK and BIO205) to begin to assemble a physical map of the region (Table 1 and FIG. 4).

TABLE 1

Genetic Markers for Positioning DDM1

| Marker | Type | Enzyme | Provided by |
|---|---|---|---|
| LFY | CAPS | RsaI | Research Genetics |
| pCITd77 | RFLP | BsaAI | A.th. Stock Ctr |
| CATHHANK | SSLP | | G. Picard |
| AB5-13 | RFLP | not tested | H. Goodman |
| g4510 | RFLP | DraI | A.th. Stock Ctr |
| cT10D21(i)2-12H3 | RFLP | XbaI | developed |
| cT10D21(i)2-5.7H3 | RFLP | XbaI | developed |
| Gap5 | CAPS | RsaI | developed |
| 105N23T7 | RFLP | BclI/ClaI | A. th Stock Ctr |
| cT10D21(i)50 | RFLP | PstI | developed |
| sT10D21Bam | RFLP | BclI | developed |
| sT8D13NcoI | RFLP | BclI/BsaAI | developed |
| Mi335 | RFLP | HindIII | C. Dean |
| 93N23T7 | RFLP | XbaI | A.th Stock Ctr |
| m555R1.4 | RFLP | DraI | H. Adler |
| m555 | CAPS | AccI/MseI | J. Bender |
| Bio205 | RFLP | DraI | B. Osborne |
| BIO205-17 | RFLP | DraI | developed |
| CD3-42 | RFLP | BglII | A.th Stock Ctr |

The table indicates the molecular markers used in the positional cloning of DDM1., their nature (RFLP = restriction fragment length polymorphism, SSLP = simple sequence length polymorphism, CAPS = cleaved amplified polymorphic sequence), the enzyme necessary to detect the polymorphism, and the provider of the clone. A.th Stock Ctr = Arabidopsis Stock Center, Ohio State University.

Figure 4:
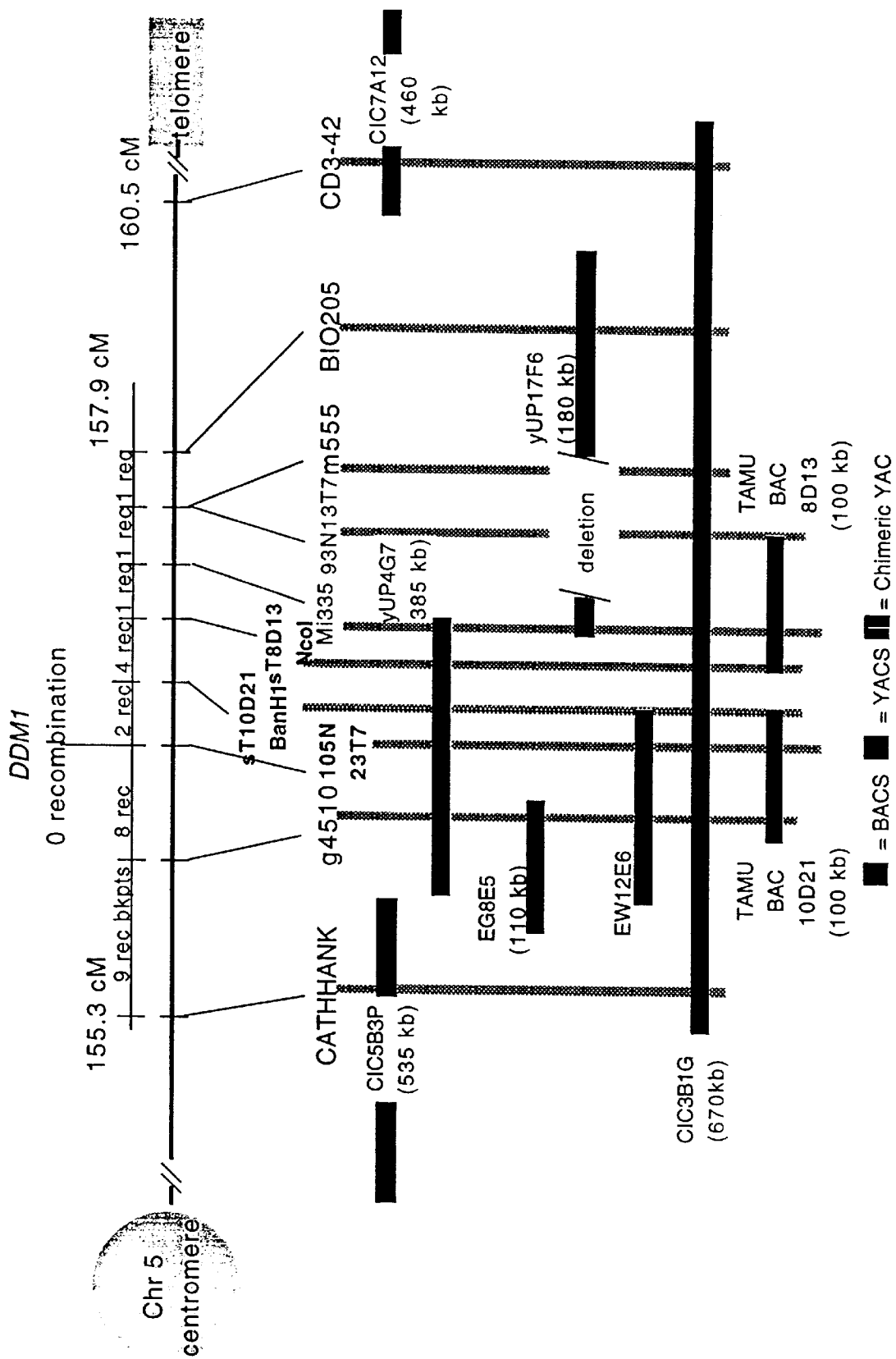
FIG. 4. Diagram showing the genetic and physical map of the DDM1 locus in Arabidopsis thaliana, at lower resolution.

BUILDING A PHYSICAL MAP OF THE DDM1 LOCUS:

A subclone of BIO205 was generated (205-17), which contained only the DNA that looked across the polymorphic DraI restriction site. Because CATHHANK was a simple sequence length polymorphism (SSLP), it would not be useful as a hybridization probe. However, the marker CATHHANK comes from an ankryin repeat clone AB5-13. Four Arabidopsis yeast artificial chromosome (YAC) libraries were screened using AB5-13 and 205-17 as hybridization probes. The CIC library, EG, EW, and yUP libraries were provided on filters in 96 well formats by the A.th Stock Center (Ohio State), and were screened simultaneously with both probes. A collection of YACs was identified and further characterized (FIG. 4). Extensive characterization of most YAC clones revealed that either the inserts were deleted, chimeric, or too large to be of use. We abandoned YACs for BACs (bacterial artificial chromosomes), which are easier to use and may possess more insert stability.

During the course of the walk, an EST RFLP marker for Succinate dehydrogenase (105N23T7) was discovered to have linkage to the bottom arm of chromosome five. We subsequently showed the marker to be very tightly linked to ddm1. Because 105N23T7 showed no recombination with ddm1 in our breakpoint lines we reasoned that the gene must be in close proximity to SuDH. Armed with a probe at molecular zero (the physical window of no recombination with ddm1) we abandoned YACs using BAC filter sets provided by Joe Ecker's group at the University of Pennsylvania, we isolated bacterial artificial chromosomes (BACs) that contained 105N23T7 by hybridization to the gridded filters in a 384 well format. Once we had collected the positive clones (~30 in total) we used Southern analysis to assay the BACs for marker content and assembled them into a contig (Table 2 and FIG. 5).

TABLE 2

YAC and BAC content (by hybridization)

| Marker:<br>Clone | CATHHANK | g4510 | 105N23 | sT10D21Bam | sT8013Nco | Mi335 | 93N13 | M555 | Bio205 | CD342 |
|---|---|---|---|---|---|---|---|---|---|---|
| yCIC3B1G | + | + | + | + | + | + | + | + | + | + |
| yCIC5B13P | + | + | | | | | | | | |
| yCIC7A12 | | | | | | | | | | + |
| yEG8E5 | + | | | | | | | | | |
| yEW12E6 | | + | + | + | + | | | | | |
| yUP17F6 | | | | | + | | + | | | |
| yUP4G7 | | + | + | + | + | + | | | | |
| bF10010 | | + | + | + | | | | | | |
| bF16H19 | | + | + | + | | | | | | |
| bF19G16 | | | + | + | | + | | | | |
| bF23A16 | | | + | + | + | | | | | |
| bF26B24 | | | + | + | | | | | | |
| bF28L19 | | + | + | | | | | | | |
| bF3L3 | | | + | + | | | | | | |
| bF4L12 | | + | + | + | | | | | | |
| bF7I18 | | + | + | + | + | | | | | |
| bF9H17 | | + | + | | | | | | | |
| BT8D13 | | | + | + | | | | | | |
| bT10D21 | | + | + | + | | | | | | |
| bT13E12 | | | + | + | + | | | | | |
| bT29C4 | + | + | | | | | | | | |

YAC clones, indicated by yXXX, and BAC clones, indicated by bXXX were assayed for content by Southern analysis with the markers indicated across the top of the table.

Figure 5:
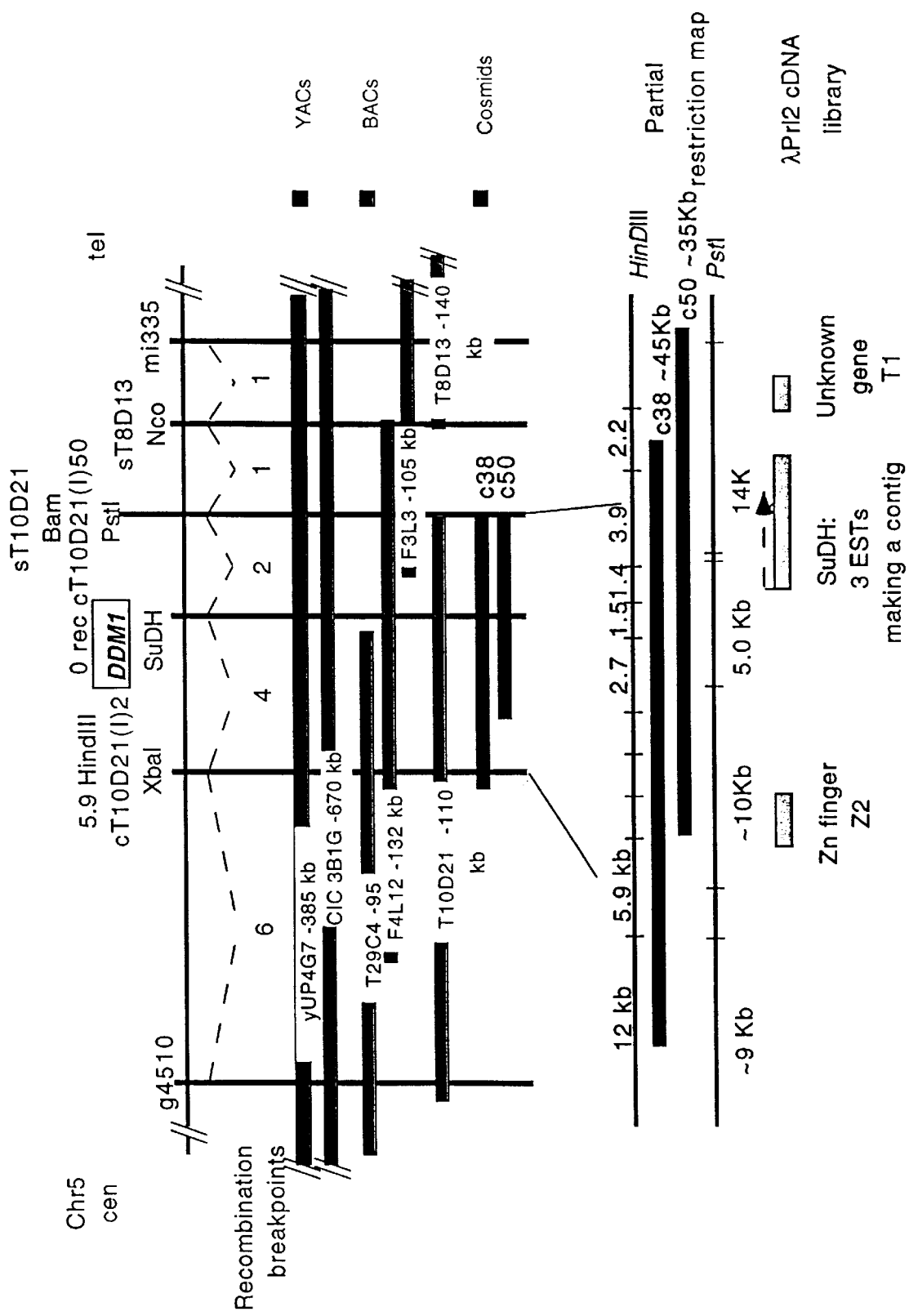
FIG. 5. Diagram showing the genetic and physical map of the DDM1 locus in Arabidopsis thaliana, at higher resolution.

The clones came from two libraries, TAMU (Texas A&M University), and IGF (Germany -Max Planck Institute). We knew that 105N23T7 was at molecular zero and that ΔG4510 (a deletion derivative of the original clone, G4510) and Mi335 were markers that flanked 105N23T7 on the centromere and telomere sides respectively (FIG. 5). From the contig we chose two BACs, T10D21 and T8D13 and made end clones for each by plasmid rescue. Each of the end clones was then used as an RFLP probe and mapped on the breakpoint lines to define the ends of the clones genetically. The results of this mapping suggested that DDM1 was entirely on T10D21. The BAC end clone sT10D21Bam mapped two recombination events to the right of ddm1. Because T10D21 contained ΔG4510, 105N23T7, and sT10D21Bam we had narrowed the gene to an approximately 110 Kb interval with 10 recombination events on the BAC. T10D21's insert was checked for chimerism and integrity by genomic Southern using six different restriction enzymes. No alterations of the insert relative to genomic DNA were found.

T10D21 was then amplified and a cosmid library was generated from the BAC using Stratagene's SuperCos vector, by cloning partially digested Sau3A1 BAC insert DNA into the BamHI site of SuperCos. Ligated products were packaged using a size selecting packaging extract (Gigapack XL -Stratagene) and infected into $E.coli$ XL1 MRA (Stratagene). Clones were inoculated into a microtiter dish and then replicated using a "hedgehog" onto a nylon filter. The colonies were screened by hybridization using 105N23T7 as a probe until about 50 positives were in hand. The positives were then cut with HindIII and BglII to fingerprint them for contig assembly and subsequently screened by Southern using the 105N23T7 probe. Two overlapping cosmid clones, C38 and C50, were selected for further analysis. Indirect end-labeling was used to generate a partial HindIII and complete PstI restriction map of both cloned inserts (FIG. 5).

To further delimit the position of the DDM1 gene, restriction fragments from C38 and C50 were used to find RFLP markers for genotypic analysis on the recombination breakpoint collection. An RFLP recognized by a 5.7 Kb HindIII fragment contained totally within C38 near it's left most boundary, mapped +4 recombination events to the left (centromeric) of ddm1. Further, C38 also contained a PstI polymorphism originally found using the whole C50 cosmid as a probe, c50PstI (Table 1). c50PstI mapped 2 recombination events to the right (telomeric) of ddm1. By restriction mapping we were able to show that this RFLP was within 4 Kb of the smallest PstI fragment inside SuDH. Based upon these data, we knew that C38 contained the DDM1 gene. In the physical interval defined by C38, ~45 Kb, the physical distance per recombination in our break points lines was 1 crossover every 7.5 Kb (45 Kb/6 breaks).

As the genetic mapping was proceeding, we began to look for cDNA clones from the region. A λ-PRL2 $A.$ $thaliana$ cDNA library (Arabidopsis stock center Ohio State) was screened for cDNAs using isolated restriction fragments from C38 (partial map FIG. 5). Four SuDH clones and one unknown cDNA, provisionally named T1, were identified by using the ~10 Kb PstI I fragment. The representation of SuDH clones in this library was 7 SuDH-hybridizing clones per 10,000 plaques screened. PstI fragment B (8.5 Kb) recognized an unknown zinc finger protein, provisionally named Z2. PstI fragment E (5.0 Kb) only identified more SuDH clones. Ti was positioned distal to SuDH and as such was excluded as a DDM1 candidate. Z2 was placed centromeric to SuDH but was located ~10 Kb away, a distance suggesting that it may not be ddm1. We were unable to generate a molecular marker for Z2 and as such were not able to map it relative to ddm1, and could not exclude it as a candidate gene. Because of the high expression levels and representation of SuDH in the cDNA library, and because development of new markers was difficult, we concluded the best approach to identify DDM1 was to sequence the entire C38 cosmid. The entire sequence would afford us all of the genes and the ability to generate molecular markers that would help further delimit the DDM1 gene.

SEQUENCING OF THE DDM1 LOCUS:

C38 DNA was amplified, purified and verified by restriction analysis. The DNA was sonicated and 1–2 Kb fragments were isolated and purified from an excised agarose gel slice. The isolated fragments were cloned into the SmaI site of M13mp18. Ligated products were electroporated into $E.$ $coli$ JS5 and plated on LB with Xgal and IPTG (for screening out clones without inserts). Positive plaques were toothpicked into $E.$ $coli$ JM101 and a library archive was created by making glycerol stocks in microtiter dishes. 645 clones were amplified and phage DNA was recovered. Sequencing was done first using the M13–21 forward primer. After assembly of the "forward" reads, clones on the 5' and 3' ends of each sequence contig were selected for "reverse" reads. Phage from the archived library from these reads were amplified and RF DNA was isolated using the Wizard spin-column miniprep kit (Promega). "Reverse" reads were sequenced from 72 double stranded RF DNA clones with the M13mp18–45 reverse primer. Sequence data were collected using an automated sequencer (both an ABI 373 and ABI 377) with the accompanying software suites for the Macintosh. Following assembly of the reverse reads, and the forward reads, six sequence contigs were formed representing almost 50 of 52 Kb (insert ~45Kb plus the cosmid vector ~7 Kb). The data set included 598 total reads from 789 total reactions (~75% success). Oligonucleotide primers were ordered to close the areas corresponding to the gaps by PCR. The order of the sequence contigs was assigned by blastx, available restriction mapping and Southern blot analysis of C38, and confirmed by PCR. The sequence gaps were closed by sequencing the PCR products corresponding to the gaps. The hole sizes were 700 bp, 600 bp, 300 bp, and 3 holes were less than 200 bp. Sequence assembly was performed using XBAP, PHRED, and PHRAP for UNIX systems, and DNASTAR (V3.0) for the Macintosh.

Figure 6:
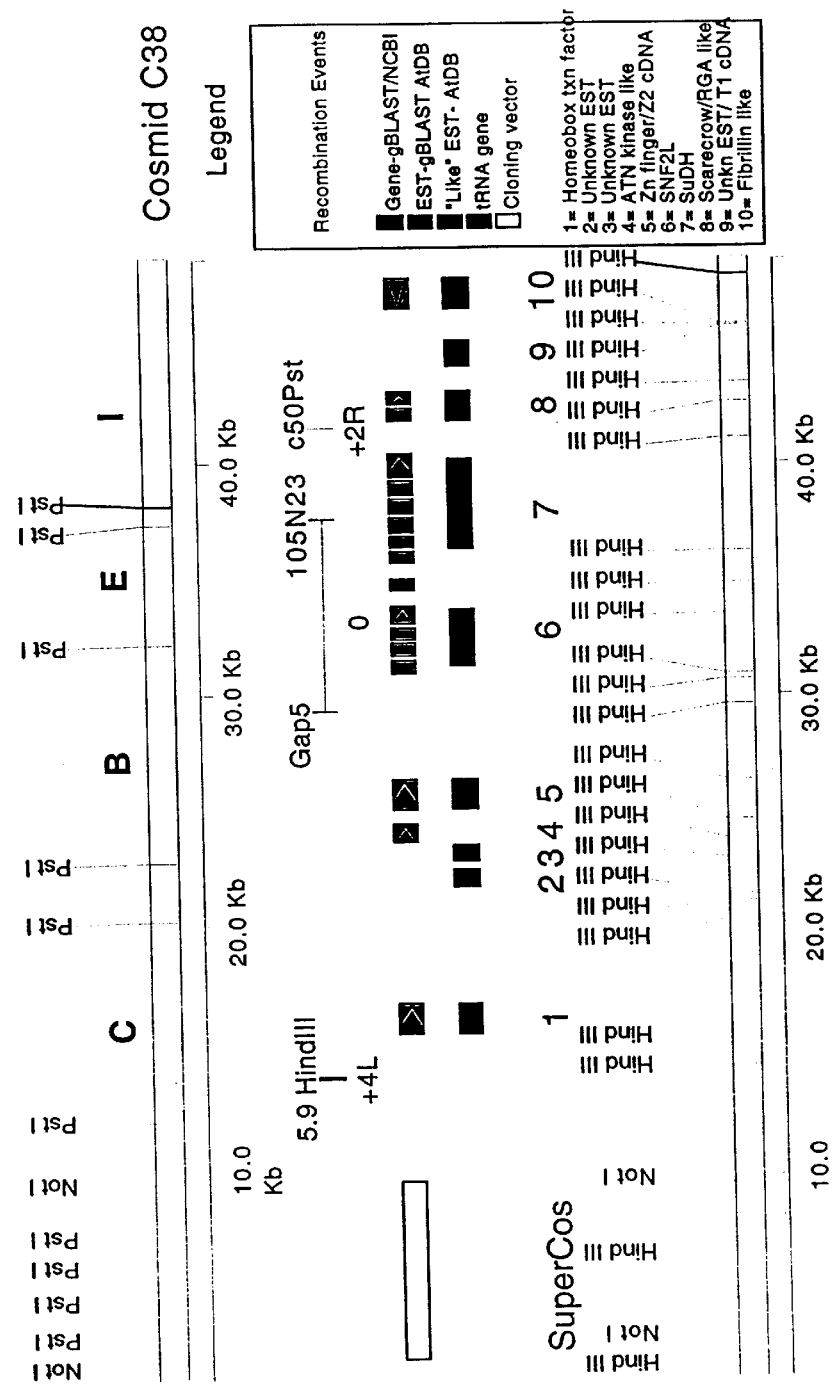
FIG. 6. Diagram showing the physical map of the DDM1 locus on cosmid C38 of the A. thaliana genomic cosmid library.
Figure 7B:
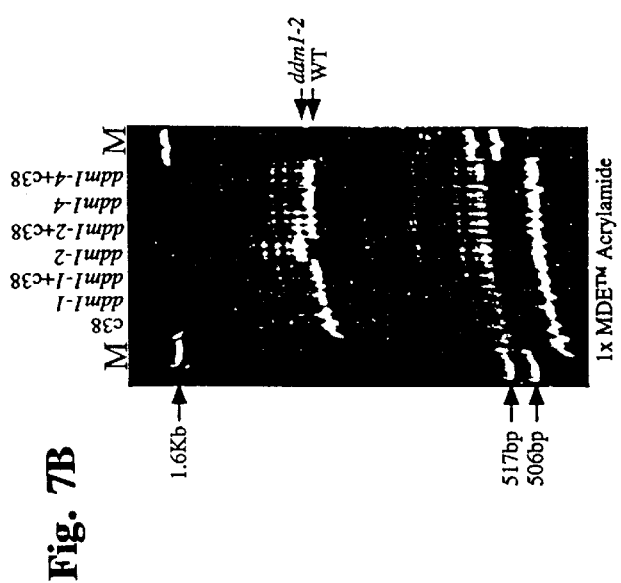
FIG. 7B: Ethidium bromide stained native polyacrylamide gel (1×MDE; FMC) containing size-fractionated RsaI restriction fragments of SNF2F–SNF2R amplicons generated by PCR using the templates indicated at the top of the gel (c38=cosmid DNA containing the region; ddm1–x=genomic DNA from indicated mutant). The PCR products were mixed as indicated, heat denatured and slowly cooled following a heteroduplex analysis protocol. The ~700 bp RsaI fragment in the ddm1-2 mutant contains a mutation leading to a change in electrophoretic mobility.
Figure 7A:
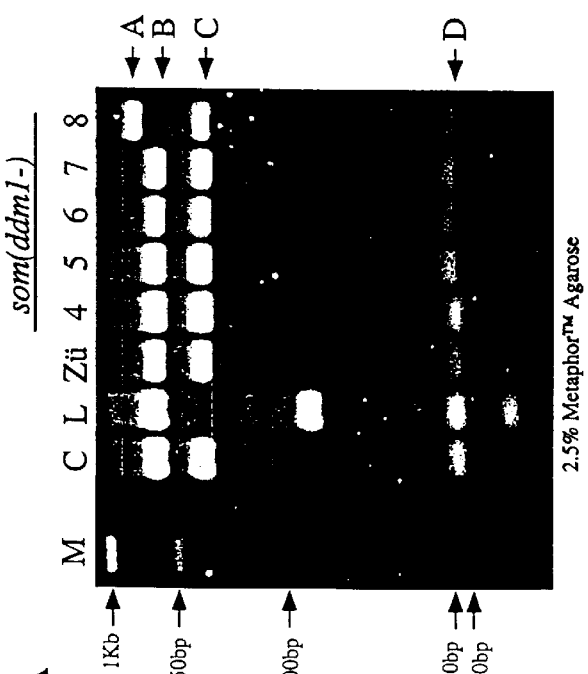
FIG. 7A: Ethidium bromide stained 2.5% agarose gel containing size-fractionated RsaI restriction fragments of 230R–354F amplicons generated by PCR using various genomic templates (C=Columbia, L=Landsberg, Zu=Zurich, som4 D som 8=DNA hypomethylation mutants in a Zu background, M=molecular weight markers). A size polymorphism is seen in the som8 sample (A vs. B) localizes the som8 mutation to the beginning of the region similar to SNF2L.

BLASTx of both NCBI/GenBank and AtDB, Genefinder and NetPlantGene searches determined that there were 10 ORFs on C38 (FIG. 6). Of these ten, at least 9 were represented in the EST library collection of Atdb, including SuDH, Z2 and T1. The organization of the genes and predicted products are (from centromere to telomere): AP2-like homeobox transcription factor, two unknown ORFs, ATN1 kinase like, Z2- Zn finger, SNF2-like (SNF2L), Glu tRNA, SuDH, Scarecrow/RGA like transcription factor, Unknown ORF, Fibrillin like gene. The genetic interval containing ddm1 contained 5 ORFs (from +4 L to +2 R FIG. 6). However, given that 4 recombination events existed centromeric to SuDH (itself at 0), and that only 4 Kb telomeric to SuDH was +2 R, we felt that by position the SNF2-like gene and Z2 were the best candidates for ddm1. Further positioning ddm1 came by finding of a RsaI CAPS in the GAP5 region (FIGS. 7, panel A). GAP5 is the ~1.7 kb that fell between the Z2 sequence contig and the SNF2L sequence contig. Scoring of the polymorphism on the recombination breakpoints revealed that GAP5 was at molecular zero as well. Therefore, the most proximal breakpoint in our collection must fall to the left of SNF2L.

IDENTIFICATION OF A DDM1 CANDIDATE GENE:

Nine candidate ddm1 alleles exist, three from our EMS collection, and 6 putative alleles identified in a screen for loss of gene silencing (ddm1=som; Mittlesten Scheid et al., Proc. Natl. Acad. Sci. USA 95: 632–637, 1998). Five of these alleles came from a fast-neutron mutagenesis, and as such were likely to contain structural rearrangements at the ddm1 locus.

Using the GAP5 primers, one of the FN candidate alleles (som8) was found to contain a ~100 bp duplication/insertion in a ~1.3 Kb RsaI fragment predicted to contain the ATG of the SNF2-like gene (by BCM Genefinder) (FIG. 7, panel A). Another mutation was detected in a RsaI digest of ddm1-2 PCR amplified DNA. The entire putative SNF2-like coding region was amplified by PCR generating a ~4 Kb fragment (primers A to SNF2R) (FIG. 7, panel B). The alteration was detected following restriction of the PCR product with RsaI using a 6% nondenaturing Mutation Detecting Enhancing (MDE™) poly-acrylamide gel (FMC). Restriction fragments were visualized by ethidium bromide fluorescence. MDE™ gels sieve not only by size but also by shape (secondary and tertiary structures) (FMC). Analysis revealed that ddm1-2 showed an alteration in a ~700 bp product from the 3' end of the SNF2-like ORF. The alteration is not evident on 2.5% or 3.5% agarose gels, suggesting that the change is not a simple duplication/insertion making the fragment larger.

Our initial mutation detection results were confirmed by subsequent sequence analysis (FIGS. 8 and 9). The som8 mutation results in an insertion of 82 base pairs directly downstream of the initiator ATG codon. The som8 mutation destroys the open reading frame of the first protein-coding exon and leads to premature termination after only 16 codons (FIG. 8). The ddm1-2 mutation is a base pair substitution (GD>A) in the splice donor site for intron 9. As shown in FIG. 9, the ddm1-2 mutations leads to an alteration in mRNA structure, most likely choice of an alternative splice donor site upstream. Both the som8 and ddm1-2 mutations are expected to destroy, or severely impair, gene function. These results identify the DDM1 gene and provide evidence that the gene is expressed.

The nucleotide sequence of the DDM1 gene from Arabidopsis thaliana is set forth below as Sequence I.D. No. 1 (SEQ ID NO:1). The DDM1 protein coding regions are at the following positions: 782–1252, 1354–1440, 1549–1895, 1976–2165, 2251–2437, 2559–2629, 2703–2892, 2975–3070, 3148–3242, 3317–3436, 3540–3659, 3745–3843, 3934–4038, 4130–4354). The tRNA-glu coding region is at positions 4826–4755. Positions 785 and 3243 are bold and underlined to indicate: (1) the som8 rearrangement, which comprises a deletion of G at 785 and an 83 bp insertion between 785 and 786 in the wild-type sequence; and (2) the ddm1-2 base pair substitution of G to A at position 3243.

TGATCATTTT CTTCCTCCGG CCAATTTGCA GATC-
GAAAAA TGATTTAGCT TTTTATTAAA AATATTGTTA
TTCGTTTTTA GCCGATATCA TAACTTTTTG AGATA-
CATTA TCAACACACT CGTGCAACTG AGATATTCTT
GACACAATTT TTGCATTTGA AATTGGCAAT TTTG-
TACTAC TCATATAGTT TGAAGCTTCA ATTCACTACA
AAGGTTATTA CTAATTGTGT CGACAAATCC AGCA-
GATTTA ATAATGCCCA TTCCATTAAA TGTTTTTTAG
TTTAATAATA GGATGATCAT ATGACCAAAA TCG-
TAAATAA GGGTTAGGGG TAAACCTGTC
ATTTCAAGCT TCCCGCCCAT GGGCGCTACT
CCCAATTTAA TAAAAAATAA GAAAATAGGC
GTAAATATGA GAGTGTGTTT TTTCAATATA
CCCTCGGTTT TGAATTTGCT CTCAAAAGCG ACG-
GAGACGA CTGTTTGGCT CGGTGATTTC TCCCGC-
CGTT TGGGTTTTTC TTACCGGAAT TTCCTTCTCC
TTCGATGGTT AGTCTGCGCT CCAGAAAAGT TAT-
TCCGTAA GTCCCTCCAC CTTTCCTTTT
CATTTCGTTA TTTCCGGCGA TTTTCTAGGT CCT-
TAACGCT CTCGAAATCG CTCGCTGTTC TTGGTG-
GTTT TTGGTTCCCT CTCTGCGTAA TTTTGTTTGT
CGTGTTTTTG GATTATATTC TCTGACTATT GGTCT-
CACTG TTGATTTATC ATTTCTCGAT TTTGGATTTT
TGGACTCTTA GGGCTTCGGA AATGGTCAGC
GACGGGAAAA CGGAGAAAGA TGCGTCTGGT GAT-
TCACCCA CTTCTGTTCT CAACGAAGAG GTTTGT-
TCTA TGTTCTACTA TTTTGCCTTC CTAGTGTGGT
TGCTTTGTGA AACTTTGTGT GTTACTCTTT
GTTTCTTTAA ATCTGGGGTG TTCTGTAAAT GGGTC-
CTTTT TGGTCCTTTT TTTCTGAATG TGAAGGAAAA
CTGTGAGGAG AAAAGTGTTA CTGTTGTAGA
GGAAGAGATA CTTCTAGCCA AAAATGGAGA TTCT-
TCTCTT ATTTCTGAAG CCATGGCTCA GGAGGAA-
GAG CAGCTGCTCA AACTTCGGGA AGATGAAGAG
AAAGCTAACA ATGCTGGATC TGCTGTTGCT
CCTAATCTGA ATGAAACTCA GTTTACTAAA
CTTGATGAGC TCTTGACGCA AACTCAGCTC
TACTCTGAGT TTCTCCTTGA GAAAATGGAG GATAT-
CACAA TTGTAATCTT CTTTATTTCT TTCTTCTTTG
TGGTTTCTCA CTTTTCGAAT GGGAGTCATT ATTCT-
TAGTT TGAACAACTT GTGGGTGAAA TTTGTTTTGC
TAGAATGGGA TAGAAAGTGA GAGCCAAAAA GCT-
GAGCCCG AGAAGACTGG TCGTGGACGC AAAA-
GAAAGG CTGCTTCTCA GTACAACAAT GTTGGT-
TCCA TTTATATAAT TTTCAACTAC TATGCATGAT
CTTGTATATA TTGTTTTTTC TGCTTGTTTG
AGAAAGTAAC TTACTTGGAT GCTTTTTTCT TCAAT-
CAGAC TAAGGCTAAG AGAGCGGTTG CTGCTAT-
GAT TTCAAGATCT AAAGAAGATG GTGAGACCAT
CAACTCAGAT CTGACAGAGG AAGAAACAGT CAT-
CAAACTG CAGAATGAAC TTTGTCCTCT TCT-
CACTGGT GGACAGTTAA AGTCTTATCA GCT-
TAAAGGT GTCAAATGGC TAATATCATT
GTGGCAGAAT GGTTTGAATG GAATATTAGC TGAT-
CAAATG GGACTTGGAA AGACGATTCA AAC-
GATCGGT TTCTTATCAC ATCTGAAAGG
GAATGGGTTG GATGGTCCAT ATCTAGTCAT TGCTC-
CACTG TCTACACTTT CAAATTGGTT CAATGAGATT
GCTAGGTACT CTCATGGCCA TATGTGTTTG TATA-
GATCCA ATGCTTTGGG GTTTCTGTTG
AAAGTTTTCT TACCTTTTCC ATTAGGTTCA CGCCT-
TCCAT CAATGCAATC ATCTACCATG GGGATAAAAA
TCAAAGGGAT GAGCTCAGGA GGAAGCACAT
GCCTAAAACT GTTGGTCCCA AGTTCCCTAT AGT-
TATTACT TCTTATGAGG TTGCCATGAA TGAT-
GCTAAA AGAATTCTGC GGCACTATCC ATG-
GAAATAT GTTGTGATTG ATGAGGTAAA
TTCCGAGATT GGTCAATGTA CTAGGCTTTG AAGAT-
CAAGA TGATCTCTCT AACTGATAAT TTTGTTCTTG
TATATTATAG GGCCACAGGT TGAAAAACCA
CAAGTGTAAA TTGTTGAGGG AACTAAAACA
CTTGAAGATG GATAACAAAC TTCTGCTGAC
AGGAACACCT CTGCAAAATA ATCTTTCTGA
GCTTTGGTCT TTGTTAAATT TTATTCTGCC TGA-
CATCTTT ACATCACATG ATGAATTTGA ATCATGG-
TAC AAACATGGTC CTTTTCTACT ATTATCCCTA
ACTAGTCTTC TTTTTTTTT TTTTTTGTT
AACACTGGTG GCAGCTTTTT GACATTTATT

CCTTTCTTAG TATCTAACTG ATAGATGAGT CTCTA-
CAGGT TTGATTTTTC TGAAAAGAAC AAAAAC-
GAAG CAACCAAGGA AGAAGAAGAG AAAAGAA-
GAG CTCAAGTATG TACAATTATA TCAATTTTCC
TTTATTTCTT TGATTGTATT TATGTCTTAT
GCTAAGGGTA CATCTTGTCT AGGTTGTTTC
CAAACTTCAT GGTATACTAC GACCATTCAT CCTTC-
GAAGA ATGAAATGTG ATGTTGAGCT CTCACTTCCA
CGGAAAAAGG AGATTATAAT GTATGCTACA
ATGACTGATC ATCAGAAAAA GTTCCAGGAA
CATCTGGTGA ATAACACGTT GGAAGCACAT CTTG-
GAGAGA ATGCCATCCG AGGTACATGA
TCTATTTTTT TTTTTAATA CTTTGTTTAA TTATGT-
CATT TTCTGCATTG ATTTGTTCAT CCCCTATACT
TCAGGTCAAG GCTGGAAGGG AAAGCTTAAC AAC-
CTGGTCA TTCAACTTCG AAAGAACTGC AACCATC-
CTG ACCTTCTCCA GGGGCAAATA GATGGTTCAT
GTATGTCAGT TTCTTTAAG AAACGTAAGA
AAAACTTCTG TCATACTGTT CTGTCTAATT
GTTTCATTTC GTGACAGATC TCTACCCTCC TGT-
TGAAGAG ATTGTTGGAC AGTGTGGTAA ATTC-
CGCTTA TTGGAGAGAT TACTTGTTCG
GTTATTTGCC AATAATCACA AAGTATGTTT
CACAAACCCA TGGCTCGTAG CTCATTTCCC
TTTGAGAACT TCTCTGATCC ATTTGCTGAT GAC-
CAGGTCC TTATCTTCTC CCAATGGACG
AAACTTTTGG ACATTATGGA TTACTACTTC AGT-
GAGAAGG GGTTTGAGGT TTGCAGAATC GATG-
GCAGTG TGAAGCTGGA TGAAAGGAGA AGACAG-
GTTT CACCTGTGCT TATGCTGCTT TTGCGTTGCT
TTTAAGCAAT ATTCTGACCA AATATTATAA CCAT-
AAGGTC TCTCTCTCTC TCTCTTTGCC TTGAAA-
CAGA TTAAAGATTT CAGTGATGAG AAGAGCAGCT
GTAGTATATT TCTCCTGAGT ACCAGAGCTG GAG-
GACTCGG AATCAATCTT ACTGCTGCTG ATACATG-
CAT CCTCTATGAC AGCGACTGGG TAATCAAATC
AATTAATTTA TTTTCTTTGA AGGAAAATCT
TTCTCTTTCG TGTTGTCTCC AACTGTGTTT TGTCT-
GATCT CCAGAACCCT CAAATGGACT TGCAAGC-
CAT GGACAGATGC CACAGAATCG GGCAGACGAA
ACCTGTTCAT GTTTATAGGC TTTCCACGGC
TCAGTCGATA GAGGTAAAAC TCTTTGTTGT
TCATATCAAT CAATCTTAAC TTCAAACCAT
TGAGATTGTT GCCTCATGAG ATTGGTTTAT
GACATTTGCT CAGACCCGGG TTCTGAAACG
AGCGTACAGT AAGCTCAAGC TGGAACATGT GGT-
TATTGGC CAAGGGCAGT TCATCAAGA ACGTGC-
CAAG TCTTCAACAC CTTTAGAGGT TTTAACTTCT
CTTAAAGCTC AATCCTTTTT AGATACACTT ATTAT-
CAACA AAATCTCCTA TTGACAGCTT GAAC-
CAAACT AACACACAGG AAGAGGACATA CTG-
GCGTTGC TTAAGGAAG ATGAAACTGC
TGAAGATAAG TTGATACAAA CCGATATAAG CGAT-
GCGGAT CTTGACAGGT TACTTGACCG GAGTGAC-
CTG ACAATTACTG CACCGGGAGA GACACAAGCT
GCTGAAGCTT TTCCAGTGAA GGGTCCAGGT TGG-
GAAGTGG TCCTGCCTAG TTCGGGAGGA ATGCT-
GTCTT CCCTGAACAG TTAGGACACA TTAATAAGCC
AGGCCTTGAA ACCACTTCTG TGTTTTTTTT
TTTTTTTCC GGAACATGAT CGGTTACTTT
TGGCTGGGAG GATTTAATTA TTAGAGGGCT
CGGAAGTTTT TGTAAGTTAA AGAACTCACT
TAAAACCCTG AAAACATGAC AGTTAATGGT GATT-
AGCTCT CAATGTGATG AAAACAATTG GCCCTCT-
GAT TTTGCTGTTG CGGTAATATT ATGACTTGTG
TACGTTATA GTCTTTGTAG TCTGCAATTT TGGCAT-
TGAG CTATTTCTCA CGAACTTATG GGATCTTATG

TTTTGGATTT GGGATTTGTT AACTTATATG ATTAG-
GCTCA ATAGTTTCAC AGAATATTAA AAACTTGAGT
AGGGTTTAAA AAAGAAGCAA AAAGCTCCGA TGC-
CGGGAAT CGAACCCGGG TCTCCTGGGT GAAAGC-
CAGA TATCCTAACC GCTGGACGAC ATCGGATTTG
TTGATGTCTA TTCTTGTAAA TAGTAAATAT
TTAGTTTTAT CGGTTTTGCA TCTAATGGAC TAAAA-
CATGA ACACGAGACG CCGACAAGAA
TGAATGGGGC AGGCACCAAA CATTTGGGTA
AAAGTATGCA GTGGGGTATT ATTGACAATT TGAC-
CATTAC AAGAGCTAAT

The deduced amino acid sequence encoded by Sequence I.D. No. 1 is set forth below as Sequence I.D. No. 2 (SEQ ID NO:2).

MVSDGKTEKD ASGDSPTSVL NEEVCSMFYY FAFV-
VWLLCE TLCVTLCFFK SGVFCKWVLF GPFFLN-
VKEN CEEKSVTVVE EEILLAKNGD SSLISEAMAQ
EEEQLLKLRE DEEKANNAGS AVAPNLNETQ
FTKLDELLTQ TQLYSEFLLE KMEDITINGI ESESQ-
KAEPE KTGRGRKRKA ASQYNNTKAK RAVAAMISRS
KEDGETINSD LTEEETVIKL QNELCPLLTG
GQLKSYQLKG VKWLISLWQN GLNGILADQM
GLGKTIQTIG FLSHLKGNGL DGPYLVIAPL STLSN-
WFNEI ARFTPSINAI IYHGDKNQRD ELRRKHMPKT
VGPKFPIVIT SYEVAMNDAK RILRHYPWKY VVIDE-
GHRLK NHKCKLLREL KHLKMDNKLL LTGT-
PLQNNL SELWSLLNFI LPDIFTSEDE FESWYKHGLI
FLKRTKTKQP RKKKRKEELK YVVSKLHGIL RPFILR-
RMKC DVELSLPRKK EIIMYATMTD HQKKFQEHLV
NNTLEAHLGE NAIRGQGWKG KLNNLVIQLR KNCN-
HPDLLQ GQIDGSYLYP PVEEIVGQCG KFRLLERLLV
RLFANNHKQV LIFSQWTKLL DIMDYYFSEK GFE-
VCRIDGS VKLDERRRQI KDFSDEKSSC SIFLLSTRAG
GLGINLTAAD TCILYDSDWN PQMDLQAMDR
CHRIGQTKPV HVYRLSTAQS IETRVLKRAY
SKLKLEEVVI GQGQFEQERA KSSTPLEEED ILA-
LLKEDET AEDKLIQTDI SDADLDRLLD RSDLTITAPG
ETQAAEAFPV KGPGWEVVLP SSGGMLSSLN S

The approximately 5 kilobases of nucleotide sequence upstream of DDM1 is set forth below as Sequence I.D. No. 3 (SEQ ID NO:3).

TGTCGGTTTCCATGGAAGATTGTGAC-
CACGACGATGAAGCTGAAGATTCTGGT-
CACGTTGAAACCTTTGTTACAGAT TTCGCAAAC-
GAATCGATTCGTTGCCATAAGTGTTTTAGGTGACA
AAGCTATCACTTCAGCGTCTGGATCTGAATTTAGAC
AATCAGTGAGAACAACTAAAAACA-
GAAAATTTCAAACTCAAAAAACA-
GAAAAAAAAAAGTTTGGATTTTTGAGAAGTACC
AGGCATTCCAGGAAGATTCCGTTTCT-
TCTTCCCGACGGATTTAGGAGTTA-
GATTTGGTTTCCGGTCGATGAGACGCTTG
CATCGCCGGAAACTGTAGAGGAAT-
TATCTAAATCAACCGGCATGTTTCAAA-
GATACTAAATTCCAATCTTTGAACACAAA AAG-
GAAGAAGCAAATCTCAGCTCAGCTCAATCTAGGG
TTTATCATCCTCCTCCTACTCTGTT-
TAGTCTCTCTTTCTCTCT CTCTTCTTCAGCTAC-
CAGTCAATCTGCTTTTCGTAAAAATCTC-
CTTTTCCCCTTTCCGCCACCAAACTTTTCTGATAACT
CACTCTCTGACCTCTCTTCTTCAAAAA-
GATTTAAAACCCCCAAAAGAAAAA-
GAAAAAAAATCAAAACTTCATTACCCAAG
AAATCTCTTAATCATTTAACCCA-
GACTCTTTCTTCTCCACACGCATCTTT-
TATCCACCGTCCACCGATCTGATCCAACGG
CTGAGATTTCACCGGAGACGAGTTATC-
CTTACTACTTCCGGCTTGTTTCTCTCT-
GAAGAATCACCGGAAAAAAAAATAAG GCGGCT-

TGTGTGTGAGACTTTGTGTGAAAGCTTCAACCTTTT
TTTTCTTTTTCTTTGGCTTGTCCAA-
GAAAAAGGAGCCT TCTTCTTCTTTTCTCTCTCTG-
GAGACAATTATAC-
TAATTTTTTCTTTTCAACTTTTCACCCTTTTTTTTT
GTTAACAA ACATTTTTTATACATAATTGTGTC-
GACTTTCAAGTTCCAAGTATCTAAATCT-
GTATTTTGGACTCCCATGCAAATAATTA AAATA-
GAATAATCTTTTGTAGATTTTAAATTGAAAACGGT
GTAGAAAGGTTAAAAGCACCAAA-
CAAAACGAGTAAATAG ATATTG-
TAATAATTTTTCACCTTTATGGAAAA-
GATTATATCATAGACGATGTACACAGATGAAAATTA
GAAAATGGCAT GTGAATATATGCAGTACCCAT-
TGAATGCAATATCAGGTTTGTAT-
TATTTTTCTATTGTATCTCTACATGTTACGTAATCA
AACGATCAAGTAATTTATTAAATATTGTC-
GATGGCGTAGAAATTATAAATTTATTT-
TATGTCATTGTTTACTATATAGATT TTGAGCTAAAC-
GACTTATTTTGTCAAAAGATATATCCGTGTTTGGTT
TAAGATTGGGTTTTAGTATTTCCAATATTAATC
TAAATTCTTAGCTTATGAACATGT-
CAATAAACAAAAAATTATTTTACTGT-
CACTGTCCTTAGACGGGGACAAAGGAGGG TAT-
TACCGTCGCGTTGTCGGACCGTAAAATAATTAACC
AAATTTTGTTGTTGAACGAATAA-
CATTTTTTACTGTGGGAAT TTGTCGTGTAGCAT-
TACGTTCGAAATCGCAATTTGTTTCT-
TCTTTGTGGGTGTATATTTCTGGTTAACGAAACTATAAC
CCAATTTAATGCAATGTTCGTCT-
GTTTTGTTGACTTTGACCCTTTTTGG-
TAATATTCGTTCAGCTTTTGTTTTAACGT TTTCAT-
TGCCTTGTAGGCATCTGAGAAGCTCAGATTCTGAC
ACGTGTCTTTTGTTATCTGAATTTG-
CATCCGTTGGATAA ACATGACGCTGACAGGTGGAT-
TGAAAAGTAACCAGCTTGGATTTCTGTG-
TATATGTTACACCGCCACTTCCCTTAATTTC
TTCGTTCTTAGTTAAAATAAAAAAGGTT-
TATTTATGAGTAAAAGTATGTAAAACGA-
CAACGAATTACTATAAGAATTAAA ATT-
TATCTTTGCTTAGTAATTTGCACTTAAGATTGGATT
CAAATTTTGTAAAAAGCGAATGTTA-
CATATATGTCCATTGA AAAAATTGCATTTGACTTTA-
CAAGCATTGAAATTAATTAATTTGGGAC-
CCCTTTTTTTGTTAGTTTCAAAGGAAGAATTA
TTTTAGGCTGAGATGGGTCCCTCCAT-
AAACTCACTATTCTGCCAGCATACAAAT-
TCCTTAACATATGGTCCAAATAGCAG TTCCAAC-
CACTAGTATCCAATAATAATCTGAACAAATTATCTT
TCTTTTTTTTTCCTGATAATCTTGTATTTGTTGTTC
AATGAGCTTAATACGTATATTAGTTAT-
GACTTATAACTAAATACTTTGACTCACT-
TGATCCGTACACATTGATTTCGTTT ATTCAAATC-
CGAACAACGTAATGATCTTTTGGGCCGAGTTATTT
GTATTCTCAACCTGAGTCCAACCATGCTTTATGGG
CTTTTCTGTTTATTTATGCATG-
TAAAGTTTATAATGCTTGCAAATAACCA-
CATATTGTGAATGTAATTACTATGATTT
AAGGGCACTGCTTTTCTGTTTTCACGT-
TGTTTTCGAAATTGCTATTGCGTGT-
GATATCTGTGTTGGACCAATTATTGAAA AGGA-
CAAGGCTGACTCTGGTTTTTAATGAGTAGTCCCCAT
GGGAGTTATGTTCATTTACCACA-
CATTTTTTTGTATAGTA TAGTATGAGTTTT-
TATTTGATATCTTTTATCTTCG-
GAAAATAAATGGTTCAAATTGTTTGTCTAAAAATG
CACACATGAA TATCTTGTGGTCTCACACAATTG-
TAGGAAACAAATTAATATTTGTTGC-
GAAAATAATGTTATTATTTTATCATACGAAAT CCTA-
GAGAAAATGGTGGCAAAAGAGGCAAAGACTAAAC
TAATGAATTTAAAATATGAAAATGATG-
GAATGACTGGTTTAC CAATATTACAGTATATTG-
TAATTTTATAAAAACGAATCCTGAAGAA-
GAGGGCAAACCCCAAGACCACGCAAATCAGTCTA
CAAATATGAAAATTTCCAATAACTA-
GAAAAACATGTGCATTTATCTTTTTC-
CATCATTCGGATTTTTACAATGGAAATTT TGAC-
CACTGAGCGCAAGTGTTATAGTATTTTATTATTATCC
AATATTAATATCATTATTCGGATCCATG-
CATTCTATATAACTATGTCCACCATCTTACTTGTGTC-
TATGTTGCAACTTCAACGTCG-
TATATATATAGGGATTGTTGTCACGAATACAAT
GCTAATTAAGGAAGATTGTGACTTCTCG-
GAAAATTTAGAACTAATTAAGAGTG-
GAACTAAAATGCCAATGAAAAATAGCCT AAAT-
CAAAGGAGAACCACAAATATAAATTGGAAGACCT
TAAAAAACAATTAAACGAGGACGAAA-
CAAATTTTGGAATCAT CAATTATACGAAAAAAA-
GAAGAAAGAAAAAAGAGGTTTCATGAAT-
CACAGTAGTGCTGACAATCTTCGAACCATTTGTGG
GTTTCATACAATCGATCACCAATAGAA-
CAAAAGAGAAACAGAGGAACAGAAA-
GAATAGAAGGAGTGGGAAGTGTATGAGG AAGCT-
GTGTCCGAACATAGACAAAGACGATGGTCTGGAG
ACGGTGTTGGAAGTTCCGATACCGGAG-
GAGATGTTTCCGG TATGGGCAACAACGTTGCACT-
TAGGTGGCAAAATATGATGACGTGGAT-
GAAAGCTCAAACGTCTGATAAATGGTCGCAAC
CGCTTATCGCCGCTCGTATCAAC-
GAGCTCCGGTTCCTTCTCTACCTCGTTG-
GCTCGCCTCTTATACCTCTCCAGGTTCAA GTCGGT-
CACTCTGTTCATAAGCCCGTCAAAGATTGCTCCAT
TGTAAGTCATTCAAAATCAATCCTTAT-
GAAAACATAACA AAGATGTTGAAAATATGATTC-
CTCTTTTTTTTTCTTTTTTTCTTTTAT-
GATCAAAACCCAAAAAAGTCATTACCCTGCT
TCGTAAGTATTCAACATAAAGTTGT-
TAATCCATGTGTTG
TACTCTGCAAGTCTGCATTACATTAT-
TCATCGTACACAGAG TCATCAACTTCAGTTTCAT-
TGTTTTTTTGCTTATGAATTACGATTG-
CAGCAAGCTTCAACGGCGAAATACATTGTACAGC
AGTACATAGCAGCGACGGGAGGACCA-
CAGGCGTTAAACGCCGTGAACAGCATGT-
GCGTCACGGGACAAGTGAAGATGACG GCGTCG-
GAGTTTCATCAAGGAGATGATTCGGGCGTTAATCT
AAAGAGCAACGACGAAATGGGTG-
GTTTCGTTTATGGCA AAAGGATCCAGATCTTTG-
GTGTTTGGAGCTCGTCGTCTCCGGTTG-
CAAAGTGGATATGTGGAAGCAACGGTCGGCTTTCA
TGGCGACATTCCTCTAACCAGCAAACTC-
CGGCGTCTACSGG
AACGCCAARACCTCTCCGCCGGTTTWTA-
CAGGTCCAATC CGGTTATTGATTTTTTTTKGATG-
TAATGTCCGGTTCTCAAAATGTTGAAC-
CGGTGGTTTATTTATTGTTTGGAGCAGGG
GTTARATCCTCGTTCGACGGCGAATCT-
GTTTCTTGACGCAAAC
GTGTATCGGAGAGAAGATAATCAACGGT-
GAGGATTGC TTTATCTTGAAACTGGAGACGAGTC-
CGGCGGTTCGAGAAGCTCAAAGCGGTC-
CGAATTTTGAGATAATTCATCACACGAT
ATGGGGTTATTTTAGTCAAAGATCGG-
GACTTTTGATTCAGTT

CGAAGATTCGCGGCTTTTGAGAATGAG-
GACCAAGGAAG ACGAAGATGTCTTCTGGGAGAC-
TAGTGCTGAGTCGGTGATGGATGATTAC-
CGATACGTTGACAATGTGAACATCGCTCAC
GGCGGGAAAACATCGGTCACGGTTTTC-
CGGTACGGTGAAGCGTCGGCGAAT-
CATCGGAGACAGATGACGGAGAAGTGGAG GATA-
GAAGAAGTTGATTTTAATGTTTGGGGTCTCTCCGTT

SNF2-like genes encode DNA-dependent ATP-hydrolyzing enzymes (with seven characteristic "helicase" domains) that function as part of chromatin remodeling complexes (Cairns et al., 1998, supra). Chromatin remodeling is the ATP dependent repositioning of nucleosomes on DNA. Generally, SNF2-like proteins act to give other proteins, such as transcription factors, access to DNA. A number of chromatin remodeling complexes have been characterized in yeast, Drosophila and mammals which have different subunit composition and diverse functional roles. Arabidopsis has many members of the SNF2-like gene family represented in the sequenced EST collection (J. A. Jeddeloh (unpublished data)). DDM1 is not in the EST database, suggesting that it is in fact a new member of the Arabidopsis SNF2-like gene family.

MODELS FOR THE ACTION OF DDM1 AS A SNF2-LIKE GENE:

Models for the action of the DDM1 gene product as a SNF2-like gene fall into two classes. The most parsimonious model is the "direct interaction" model. Under the "direct interaction" model DDM1 acts to give DNMTase access to cytosines, perhaps by pushing nucleosomes out of the way of the methyltransferase. In this scenario, mutations in DDM1 would lead to hypomethylation directly, and the phenotypic effects of ddm1 mutations would result from methylation loss. Alternatively, DDM1 may act to establish chromatin identity, (for example, by facilitating heterochromatin assembly) which subsequently dictates the interaction with the DNA methylation system. In this model, ddm1 mutations would lead to a loss of chromatin identity, creating an unrecognizable/unmethylatable template for the DNMTase. Under the "chromatin identity" model, ddm1 mutations compromise a determinate of chromatin structure, such as histone acetylation state, and the loss of methylation is a secondary consequence of the primary change in chromatin identity. A SNF2-like gene function (ISWI) is believed to associate with histone deacetylase (Martinez-Balbas, M. A. et al., Proc. Natl. Acad. Sci. USA 95: 132–137, 1998). If DNA methylation and histone deacetylation lie in the same pathway, as suggested by the findings of Chen and Pikaard (Chen & Pikaard, Genes & Devel. 11: 2124–2136, 1997), then perhaps DDM1 mediates the interaction between the two processes.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

SEQUENCE LISTING

```
<160> NUMBER OF SEQ ID NOS: 3

<210> SEQ ID NO 1
<211> LENGTH: 5000
<212> TYPE: DNA
<213> ORGANISM: Arabidopsis thaliana
<220> FEATURE:
<221> NAME/KEY: CDS
<222> LOCATION: (782)...(1252)
<221> NAME/KEY: CDS
<222> LOCATION: (1354)...(1440)
<221> NAME/KEY: CDS
<222> LOCATION: (1549)...(1895)
<221> NAME/KEY: CDS
<222> LOCATION: (1976)...(2165)
<221> NAME/KEY: CDS
<222> LOCATION: (2251)...(2437)
<221> NAME/KEY: CDS
<222> LOCATION: (2559)...(2629)
<221> NAME/KEY: CDS
<222> LOCATION: (2703)...(2892)
<221> NAME/KEY: CDS
<222> LOCATION: (2975)...(3070)
<221> NAME/KEY: CDS
<222> LOCATION: (3148)...(3242)
<221> NAME/KEY: CDS
<222> LOCATION: (3317)...(3436)
<221> NAME/KEY: CDS
<222> LOCATION: (3540)...(3659)
<221> NAME/KEY: CDS
<222> LOCATION: (3745)...(3843)
<221> NAME/KEY: CDS
<222> LOCATION: (3934)...(4038)
<221> NAME/KEY: CDS
<222> LOCATION: (4130)...(4354)
<221> NAME/KEY: CDS
<222> LOCATION: (4826)...(4755)
<223> OTHER INFORMATION: t-RNA-glu coding region
```

-continued

```
<220> FEATURE:
<221> NAME/KEY: mutation
<222> LOCATION: (785)...(786)
<223> OTHER INFORMATION: som8 rearrangement, deletion of G at 785 and
      insertion of 83 bp between 785 and 786
<220> FEATURE:
<221> NAME/KEY: mutation
<222> LOCATION: (3243)...(3243)
<223> OTHER INFORMATION: ddm1-2 base pair substitution of G to A

<400> SEQUENCE: 1
tgatcatttt cttcctccgg ccaatttgca gatcgaaaaa tgatttagct ttttattaaa     60
aatattgtta ttcgtttta gccgatatca taacttttg agatacatta tcaacacact    120
cgtgcaactg agatattctt gacacaattt ttgcatttga aattggcaat tttgtactac    180
tcatatagtt tgaagcttca attcactaca aaggttatta ctaattgtgt cgacaaatcc    240
agcagattta ataatgccca ttccattaaa tgtttttag tttaataata ggatgatcat    300
atgaccaaaa tcgtaaataa gggttagggg taaacctgtc atttcaagct tcccgcccat    360
gggcgctact cccaatttaa taaaaaataa gaaataggc gtaaatatga gagtgtgttt    420
tttcaatata ccctcggttt tgaatttgct ctcaaaagcg acggagacga ctgtttggct    480
cggtgatttc tcccgccgtt tgggttttc ttaccggaat ttccttctcc ttcgatggtt    540
agtctgcgct ccagaaaagt tattccgtaa gtccctccac ctttcctttt catttcgtta    600
tttccggcga ttttctaggt ccttaacgct ctcgaaatcg ctcgctgttc ttggtggttt    660
ttggttccct ctctgcgtaa ttttgtttgt cgtgttttg gattatattc tctgactatt    720
ggtctcactg ttgatttatc atttctcgat tttggatttt tggactctta gggcttcgga    780
aatggtcagc gacgggaaaa cggagaaaga tgcgtctggt gattcaccca cttctgttct    840
caacgaagag gtttgttcta tgttctacta ttttgccttc gtagtgtggt tgctttgtga    900
aactttgtgt gttactcttt gtttctttaa atctggggtg ttctgtaaat gggtcctttt    960
tggtcctttt tttctgaatg tgaaggaaaa ctgtgaggag aaaagtgtta ctgttgtaga   1020
ggaagagata cttctagcca aaaatggaga ttcttctctt atttctgaag ccatggctca   1080
ggaggaagag cagctgctca aacttcggga agatgaagag aaagctaaca atgctggatc   1140
tgctgttgct cctaatctga atgaaactca gtttactaaa cttgatgagc tcttgacgca   1200
aactcagctc tactctgagt ttctccttga gaaaatggag gatatcacaa ttgtaatctt   1260
ctttatttct ttcttctttg tggtttctca cttttcgaat gggagtcatt attcttagtt   1320
tgaacaactt gtgggtgaaa tttgttttgc tagaatggga tagaaagtga gagccaaaaa   1380
gctgagcccg agaagactgg tcgtggacgc aaaagaaagg ctgcttctca gtacaacaat   1440
gttggttcca tttatataat tttcaactac tatgcatgat cttgtatata ttgttttttc   1500
tgcttgtttg agaaagtaac ttacttggat gcttttttct tcaatcagac taaggctaag   1560
agagcggttg ctgctatgat ttcaagatct aaagaagatg gtgagaccat caactcagat   1620
ctgacagagg aagaaacagt catcaaactg cagaatgaac tttgtcctct tctcactggt   1680
ggacagttaa agtcttatca gcttaaaggt gtcaaatggc taatatcatt gtggcagaat   1740
ggtttgaatg gaatattagc tgatcaaatg ggacttggaa agacgattca aacgatcggt   1800
ttcttatcac atctgaaagg gaatgggttg gatggtccat atctagtcat tgctccactg   1860
tctacacttt caaattggtt caatgagatt gctaggtact ctcatggcca tatgtgtttg   1920
tatagatcca atgctttggg gtttctgttg aaagttttct tacctttcc attaggttca   1980 cgccttccat caatgcaatc atctaccatg gggataaaaa tcaaagggat gagctcagga   2040
```

```
ggaagcacat gcctaaaact gttggtccca agttccctat agttattact tcttatgagg    2100
ttgccatgaa tgatgctaaa agaattctgc ggcactatcc atggaaatat gttgtgattg    2160
atgaggtaaa ttccgagatt ggtcaatgta ctaggctttg aagatcaaga tgatctctct    2220
aactgataat tttgttcttg tatattatag ggccacaggt tgaaaaacca caagtgtaaa    2280
ttgttgaggg aactaaaaca cttgaagatg gataacaaac ttctgctgac aggaacacct    2340
ctgcaaaata atcttctga gctttggtct ttgttaaatt ttattctgcc tgacatcttt    2400
acatcacatg atgaatttga atcatggtac aaacatggtc cttttctact attatcccta    2460
actagtcttc tttttttttt ttttttgtt aacactggtg gcagctttt gacatttatt    2520 cctttcttag tatctaactg atagatgagt ctctacaggt ttgattttc tgaaaagaac    2580 aaaaacgaag caaccaagga agaagaagag aaagaagag ctcaagtatg tacaattata    2640 tcaatttcc tttatttctt tgattgtatt tatgtcttat gctaaggta catccttgtct    2700 aggttgtttc caaacttcat ggtatactac gaccattcat ccttcgaaga atgaaatgtg    2760
atgttgagct ctcacttcca cggaaaaagg agattataat gtatgctaca atgactgatc    2820
atcagaaaaa gttccaggaa catctggtga ataacacgtt ggaagcacat cttggagaga    2880
atgccatccg aggtacatga tctattttt ttttttaata ctttgtttaa ttatgtcatt    2940
ttctgcattg atttgttcat cccctatact tcaggtcaag gctggaaggg aaagcttaac    3000
aacctggtca ttcaacttcg aaagaactgc aaccatcctg accttctcca ggggcaaata    3060
gatggttcat gtatgtcagt ttcttttaag aaacgtaaga aaaacttctg tcatactgtt    3120
ctgtctaatt gtttcatttc gtgacagatc tctaccctcc tgttgaagag attgttggac    3180
agtgtggtaa attccgctta ttggagagat tacttgttcg gttatttgcc aataatcaca    3240
aagtatgttt cacaaaccca tggctcgtag ctcatttccc tttgagaact tctctgatcc    3300
atttgctgat gaccaggtcc ttatcttctc ccaatggacg aaacttttgg acattatgga    3360
ttactacttc agtgagaagg ggtttgaggt ttgcagaatc gatggcagtg tgaagctgga    3420
tgaaaggaga agacaggttt cacctgtgct tatgctgctt ttgcgttgct tttaagcaat    3480
attctgacca aatattataa ccataaggtc tctctctctc tctctttgcc ttgaaacaga    3540
ttaaagattt cagtgatgag aagagcagct gtagtatatt tctcctgagt accagagctg    3600
gaggactcgg aatcaatctt actgctgctg atacatgcat cctctatgac agcgactggg    3660
taatcaaatc aattaattta ttttctttga aggaaaatct ttctcttttcg tgttgtctcc    3720 aactgtgttt tgtctgatct ccagaaccct caaatggact tgcaagccat ggacagatgc    3780
cacagaatcg ggcagacgaa acctgttcat gtttataggc tttccacggc tcagtcgata    3840
gaggtaaaac tctttgttgt tcatatcaat caatcttaac ttcaaaccat tgagattgtt    3900
gcctcatgag attggtttat gacatttgct cagacccggg ttctgaaacg agcgtacagt    3960
aagctcaagc tggaacatgt ggttattggc caagggcagt ttcatcaaga acgtgccaag    4020
tcttcaacac ctttagaggt tttaacttct cttaaagctc aatccttttt agatacactt    4080
attatcaaca aaatctccta ttgacagctt gaaccaaact aacacacagg aagaggacat    4140
actggcgttg cttaaggaag atgaaactgc tgaagataag ttgatacaaa ccgatataag    4200
cgatgcggat cttgacaggt tacttgaccg gagtgacctg acaattactg caccgggaga    4260
gacacaagct gctgaagctt ttccagtgaa gggtccaggt tgggaagtgg tcctgcctag    4320
ttcgggagga atgctgtctt ccctgaacag ttaggacaca ttaataagcc aggccttgaa    4380
```

-continued

```
accacttctg tgttttttt ttttttttcc ggaacatgat cggttacttt tggctgggag    4440
gatttaatta ttagagggct cggaagtttt tgtaagttaa agaactcact taaaaccctg    4500
aaaacatgac agttaatggt gattagctct caatgtgatg aaaacaattg gccctctgat    4560
tttgctgttg cggtaatatt atgacttgtg tacgtttata gtctttgtag tctgcaattt    4620
tggcattgag ctatttctca cgaacttatg ggatcttatg ttttggattt gggatttgtt    4680
aacttatatg attaggctca atagtttcac agaatattaa aaacttgagt agggtttaaa    4740
aaagaagcaa aaagctccga tgccgggaat cgaacccggg tctcctgggt gaaagccaga    4800
tatcctaacc gctggacgac atcggatttg ttgatgtcta ttcttgtaaa tagtaaatat    4860
ttagttttat cggttttgca tctaatggac taaaacatga acacgagacg ccgacaagaa    4920
tgaatggggc aggcaccaaa catttgggta aaagtatgca gtggggtatt attgacaatt    4980
tgaccattac aagagctaat                                                5000
```

<210> SEQ ID NO 2
<211> LENGTH: 801
<212> TYPE: PRT
<213> ORGANISM: Arabidopsis thaliana

<400> SEQUENCE: 2

```
Met Val Ser Asp Gly Lys Thr Glu Lys Asp Ala Ser Gly Asp Ser Pro
 1               5                  10                  15

Thr Ser Val Leu Asn Glu Glu Val Cys Ser Met Phe Tyr Tyr Phe Ala
            20                  25                  30

Phe Val Val Trp Leu Leu Cys Glu Thr Leu Cys Val Thr Leu Cys Phe
        35                  40                  45

Phe Lys Ser Gly Val Phe Cys Lys Trp Val Leu Phe Gly Pro Phe Phe
    50                  55                  60

Leu Asn Val Lys Glu Asn Cys Glu Glu Lys Ser Val Thr Val Val Glu
65                  70                  75                  80

Glu Glu Ile Leu Leu Ala Lys Asn Gly Asp Ser Ser Leu Ile Ser Glu
                85                  90                  95

Ala Met Ala Gln Glu Glu Gln Leu Leu Lys Leu Arg Glu Asp Glu
            100                 105                 110

Glu Lys Ala Asn Asn Ala Gly Ser Ala Val Ala Pro Asn Leu Asn Glu
        115                 120                 125

Thr Gln Phe Thr Lys Leu Asp Glu Leu Leu Thr Gln Thr Gln Leu Tyr
    130                 135                 140

Ser Glu Phe Leu Leu Glu Lys Met Glu Asp Ile Thr Ile Asn Gly Ile
145                 150                 155                 160

Glu Ser Glu Ser Gln Lys Ala Glu Pro Glu Lys Thr Gly Arg Gly Arg
                165                 170                 175

Lys Arg Lys Ala Ala Ser Gln Tyr Asn Asn Thr Lys Ala Lys Arg Ala
            180                 185                 190

Val Ala Ala Met Ile Ser Arg Ser Lys Glu Asp Gly Glu Thr Ile Asn
        195                 200                 205

Ser Asp Leu Thr Glu Glu Thr Val Ile Lys Leu Gln Asn Glu Leu
    210                 215                 220

Cys Pro Leu Leu Thr Gly Gly Gln Leu Ser Tyr Gln Leu Lys Gly
225                 230                 235                 240

Val Lys Trp Leu Ile Ser Leu Trp Gln Asn Gly Leu Asn Gly Ile Leu
                245                 250                 255

Ala Asp Gln Met Gly Leu Gly Lys Thr Ile Gln Thr Ile Gly Phe Leu
```

-continued

```
                 260                 265                 270
Ser His Leu Lys Gly Asn Gly Leu Asp Gly Pro Tyr Leu Val Ile Ala
             275                 280                 285

Pro Leu Ser Thr Leu Ser Asn Trp Phe Asn Glu Ile Ala Arg Phe Thr
         290                 295                 300

Pro Ser Ile Asn Ala Ile Ile Tyr His Gly Asp Lys Asn Gln Arg Asp
305                 310                 315                 320

Glu Leu Arg Arg Lys His Met Pro Lys Thr Val Gly Pro Lys Phe Pro
                 325                 330                 335

Ile Val Ile Thr Ser Tyr Glu Val Ala Met Asn Asp Ala Lys Arg Ile
             340                 345                 350

Leu Arg His Tyr Pro Trp Lys Tyr Val Val Ile Asp Glu Gly His Arg
         355                 360                 365

Leu Lys Asn His Lys Cys Lys Leu Arg Glu Leu Lys His Leu Lys
     370                 375                 380

Met Asp Asn Lys Leu Leu Leu Thr Gly Thr Pro Leu Gln Asn Asn Leu
385                 390                 395                 400

Ser Glu Leu Trp Ser Leu Leu Asn Phe Ile Leu Pro Asp Ile Phe Thr
                 405                 410                 415

Ser His Asp Glu Phe Glu Ser Trp Tyr Lys His Gly Leu Ile Phe Leu
             420                 425                 430

Lys Arg Thr Lys Thr Lys Gln Pro Arg Lys Lys Arg Lys Glu Glu
         435                 440                 445

Leu Lys Tyr Val Val Ser Lys Leu His Gly Ile Leu Arg Pro Phe Ile
     450                 455                 460

Leu Arg Arg Met Lys Cys Asp Val Glu Leu Ser Leu Pro Arg Lys Lys
465                 470                 475                 480

Glu Ile Ile Met Tyr Ala Thr Met Thr Asp His Gln Lys Lys Phe Gln
                 485                 490                 495

Glu His Leu Val Asn Asn Thr Leu Glu Ala His Leu Gly Glu Asn Ala
             500                 505                 510

Ile Arg Gly Gln Gly Trp Lys Gly Lys Leu Asn Asn Leu Val Ile Gln
         515                 520                 525

Leu Arg Lys Asn Cys Asn His Pro Asp Leu Leu Gln Gly Gln Ile Asp
     530                 535                 540

Gly Ser Tyr Leu Tyr Pro Pro Val Glu Glu Ile Val Gly Gln Cys Gly
545                 550                 555                 560

Lys Phe Arg Leu Leu Glu Arg Leu Leu Val Arg Leu Phe Ala Asn Asn
                 565                 570                 575

His Lys Gln Val Leu Ile Phe Ser Gln Trp Thr Lys Leu Leu Asp Ile
             580                 585                 590

Met Asp Tyr Tyr Phe Ser Glu Lys Gly Phe Glu Val Cys Arg Ile Asp
         595                 600                 605

Gly Ser Val Lys Leu Asp Glu Arg Arg Gln Ile Lys Asp Phe Ser
     610                 615                 620

Asp Glu Lys Ser Ser Cys Ser Ile Phe Leu Leu Ser Thr Arg Ala Gly
625                 630                 635                 640

Gly Leu Gly Ile Asn Leu Thr Ala Ala Asp Thr Cys Ile Leu Tyr Asp
                 645                 650                 655

Ser Asp Trp Asn Pro Gln Met Asp Leu Gln Ala Met Asp Arg Cys His
             660                 665                 670

Arg Ile Gly Gln Thr Lys Pro Val His Val Tyr Arg Leu Ser Thr Ala
         675                 680                 685
```

-continued

```
Gln Ser Ile Glu Thr Arg Val Leu Lys Arg Ala Tyr Ser Lys Leu Lys
    690                 695                 700
Leu Glu His Val Val Ile Gly Gln Gly Gln Phe His Gln Glu Arg Ala
705                 710                 715                 720
Lys Ser Ser Thr Pro Leu Glu Glu Asp Ile Leu Ala Leu Leu Lys
                725                 730                 735
Glu Asp Glu Thr Ala Glu Asp Lys Leu Ile Gln Thr Asp Ile Ser Asp
            740                 745                 750
Ala Asp Leu Asp Arg Leu Leu Asp Arg Ser Asp Leu Thr Ile Thr Ala
        755                 760                 765
Pro Gly Glu Thr Gln Ala Ala Glu Ala Phe Pro Val Lys Gly Pro Gly
    770                 775                 780
Trp Glu Val Val Leu Pro Ser Ser Gly Gly Met Leu Ser Ser Leu Asn
785                 790                 795                 800
Ser
```

<210> SEQ ID NO 3
<211> LENGTH: 5000
<212> TYPE: DNA
<213> ORGANISM: Arabidopsis thaliana

<400> SEQUENCE: 3

```
tgtcgaagtt tccatggaag attgtgacca cgacgatgaa gctgaagatt ctggtcacgt    60
tgaaaacctt tgttacagat ttcgcaaacg aatcgattcg ttgccataag tgttttaggt   120
gacaaagcta tcacttcagc gtctggatct gaatttagac aatcagtgag aacaactaaa   180
aacagaaaat ttcaaactca aaaacagaaa aaaaaaagt ttggattttt gagaagtacc   240
aggcattcca ggaagattcc gtttcttctt cccgacggat ttaggagtta gattttggtt   300
tccggtcgat gagacgcttg catcgccgga aactgtagag gaattatcta aatcaaccgg   360
catgtttcaa agatactaaa ttccaatctt tgaacacaaa aggaagaag caaatctcag   420
ctcagctcaa tctagggttt atcatcctcc tcctactctg tttagtctct ctttctctct   480
ctcttcttca gctaccagtc aatctgcttt tcgtaaaaat ctccttttcc cctttccgcc   540
accaaacttt tctgataact cactctctga cctctcttct tcaaaaagat ttaaaacccc   600
caaagaaaa agaaaaaaaa tcaaaacttc attacccaag aaatctctta atcatttaac   660
ccagactctt tcttctccac acgcatcttt tatccaccgt ccaccgatct gatccaacgg   720
ctgagatttc accggagacg agttatcctt actacttccg gcttgtttct ctctgaagaa   780
tcaccggaaa aaaaataag gcggcttgtg tgtgagactt tgtgtgaaag cttcaacctt   840
ttttttcttt ttctttggct tgtccaagaa aaaggagcct tcttcttctt ttctctctct   900
ggagacaatt atactaattt ttttctttc aacttttcac ccttttttt ttgttaacaa   960
acattttta tacataattg tgtcgacttt caagttccaa gtatctaaat ctgtattttg  1020
gactcccatg caaataatta aaatagaata atcttttgt agatttaaa ttgaaaacgg  1080
tgtagaaagg ttaaaagcac caaacaaaac gagtaaatag atattgtaat aatttttca  1140
cctttatgga aaagattata tcatagacga tgtacacaga tgaaaattag aaaatggcat  1200
gtgaatatat gcagtaccca atgaatgcaa tatcaggttt gtattatttt tctattgtat  1260
ctctacatgt tacgtaatca aacgatcaag taatttatta atattgtcga tggcgtagaa  1320
attataaatt tattttatgt cattgtttac tatatagatt ttgagctaaa cgacttattt  1380
tgtcaaaaga tatatccgtg tttggtttaa gattgggttt tagtatttcc aatattaatc  1440
```

```
taaattctta gcttatgaac atgtcaataa acaaaaaaat tatttactg tcactgtcct    1500 tagacgggga caaggagggg tattaccgtc gcgttgtcgg accgtaaaat aattaaccaa    1560
attttgttgt tgaacgaata acatttttta ctgtgggaat ttgtcgtgta gcattacgtt    1620
cgaaatcgca atttgttttc ttctttgtgg gtgtatattt ctggttaacg aaactataac    1680
ccaatttaat gcaatgttcg tctgtttttg ttgactttga ccctttttg gtaatattcg     1740 ttcagctttt gttttaacgt tttcattgcc ttgtaggcat ctgagaagct cagattctga    1800
cacgtgtctt ttgttatctg aatttgcatc cgttggataa acatgacgct gacaggtgga    1860
ttgaaaagta accagcttgg atttctgtgt atatgttaca ccgccacttc ccttaatttc    1920
ttcgttctta gttaaaataa aaaggttta atttatgagt aaaagtatgt aaaacgacaa     1980
cgattactat aagaattaaa atttatcttt gcttagtaat ttgcacttaa gattggattc    2040
aaattttgta aaaagcgaat gttacatata tgtccattga aaaaattgca tttgactta     2100 caagcattga aattaattaa tttgggaccc cttttttgt tagtttcaaa ggaagaatta     2160
ttttaggctg agatgggtcc ctccataaac tcactattct gccagcatac aaattcctta   2220
acatatggtc caaatagcag ttccaaccac tagtatccaa taataatctg aacaaattat    2280
cttctttttt ttttcctgat aatcttgtat ttgtttgttc aatgagctta atacgtatat    2340
tagttatgac ttataactaa atactttgac tcacttgatc cgtacacatt gatttcgttt    2400
attcaaatcc gaacaacgta atgatctttt tgggccgagt tatttgtatt ctcaacctga    2460
gtccaaccat gctttatggg cttttctgtt tatttatgca tgtaaagttt ataatgcttg    2520
caaataacca catattgtat gaatgtaatt actatgattt aagggcactg cttttctgtt   2580
ttcacgttgt tttcgaaatt gctattgcgt gtgatatctg tgttggacca attattgaaa    2640
aggacaaggc tgactctggt ttttaatgag tagtccccat gggagttatg ttcatttacc    2700 acacatttt ttgtatagta tagtatgagt ttttatttga tatcttttat cttcggaaaa     2760
taaatggttc aaattgtttg tctaaaaatg cacacatgaa tatcttgtgg tctcacacaa    2820
ttgtaggaaa caaattaata tttgttgcga aaataatgtt attattttat catacgaaat    2880
cctagagaaa atggtggcaa aagaggcaaa gactaaacta atgaatttaa aatatgaaaa    2940
tgatggaatg actggtttac caatattaca gtatattgta atttataaa aacgaatcct     3000 gaagaagagg gcaaaccca agaccacgca atcagtcta caaatatgaa aatttccaat     3060
aactagaaaa acatgtgcat ttatcttttt ccatcattcg gattttaca atggaaattt     3120 tgaccactga gcgcaagtgt tatagtattt tattattatc caatattaat atcattattc    3180
ggatccatgc attctatata actatgtcca ccatcttact tgtgtctatg ttgcaacttc    3240
aacgtcgtat atatataggg attgttgtca cgaatacaat gctaattaag gaagattgtg    3300
acttctcgga aaatttagaa ctaattaaga gtggaactaa aatgccaatg aaaatagcct    3360
aaatcaaagg agaaccacaa atataaattg gaagacctta aaaacaatt aaacgaggac     3420 gaaacaaatt ttggaatcat caattatacg aaaaaaagaa gaaagaaaaa agaggtttca    3480
tgaatcacag tagtgctgac aatcttcgaa ccatttgtgg gtttcataca atcgatcacc    3540
aatagaacaa aagagaaaca gaggaacaga agaatagaa ggagtgggaa gtgtatgagg     3600
aagctgtgtc cgaacataga caaagacgat ggtctggaga cggtgttgga agttccgata    3660
ccggaggaga tgttttccgg tatgggcaac aacgttgcac ttaggtggca aaatatgatg    3720
acgtggatga aagctcaaac gtctgataaa tggtcgcaac cgcttatcgc cgctcgtatc    3780
```

```
aacgagctcc ggttccttct ctacctcgtt ggctcgcctc ttatacctct ccaggttcaa    3840
gtcggtcact ctgttcataa gcccgtcaaa gattgctcca ttgtaagtca ttcaaaatca    3900
atccttatga aaacataaca aagatgttga aaatatgatt cctcttttt ttttcttttt     3960 ttcttttatg atcaaaaccc aaaaaagtca ttaccctgct tcgtaagtat tcaacataaa    4020
gttgttaatc catgtgttgt actctgcaag tctgcattac attattcatc gtacacagag    4080
tcatcaactt cagtttcatt gttttttgc ttatgaatta cgattgcagc aagcttcaac     4140
ggcgaaatac attgtacagc agtacatagc agcgacggga ggaccacagg cgttaaacgc    4200
cgtgaacagc atgtgcgtca cgggacaagt gaagatgacg gcgtcggagt ttcatcaagg    4260
agatgattcg ggcgttaatc taaagagcaa cgacgaaatg ggtggtttcg ttttatggca    4320
aaaggatcca gatctttggt gtttggagct cgtcgtctcc ggttgcaaag tggatatgtg    4380
gaagcaacgg tcggctttca tggcgacatt cctctaacca gcaaactccg gcgtctacsg    4440
gaacgccaar acctctccgc cggtttwtac aggtccaatc cggttattga ttttttttk     4500 gatgtaatgt ccggttctca aaatgttgaa ccggtggttt atttattgtt tggagcaggg    4560
gttaratcct cgttcgacgg cgaatctgtt tcttgacgca aacgtgtatc ggagagaaga    4620
taatcaacgg tgaggattgc tttatcttga aactggagac gagtccggcg gttcgagaag    4680
ctcaaagcgg tccgaatttt gagataattc atcacacgat atgggttat tttagtcaaa     4740 gatcgggact tttgattcag ttcgaagatt cgcggctttt gagaatgagg accaaggaag    4800
acgaagatgt cttctgggag actagtgctg agtcggtgat ggatgattac cgatacgttg    4860
acaatgtgaa catcgctcac ggcgggaaaa catcggtcac ggttttccgg tacggtgaag    4920
cgtcggcgaa tcatcggaga cagatgacgg agaagtggag gatagaagaa gttgatttta    4980
atgtttgggg tctctccgtt                                                5000
```

Figure 7C:
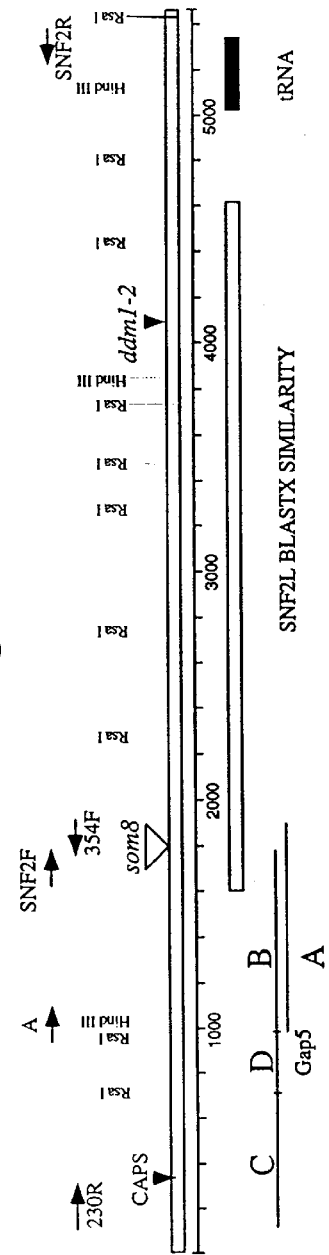
FIG. 7C: A map of the region indicating the position of oligonucleotide primers (230R, A, SNF2F, 354F, & SNF2R). The identity of RsaI restriction fragments from the 230R–354F amplicon are shown at the lower right. The approximate positions of the som8 and ddm1-2 lesion are indicated above the map, and the genomic region similar to SNF2L is shown by the shaded box beneath the map.

What is claimed is:

1. An isolated nucleic acid molecule comprising a gene located on *Arabidopsis thaliana* chromosome 5, lower arm, said gene occupying a segment of said chromosome 5, lower arm, flanked on the centromeric side within 20 kilobases by a gene encoding a zinc-finger protein and on the telomeric side within 1 kilobase by a gene encoding a glutamic acid tRNA, said gene having a restriction endonuclease cleavage map as shown in FIG. 7C.

2. The nucleic acid molecule of claim 1, wherein said gene is composed of exons that form an open reading frame having a sequence that encodes a polypeptide about 750–850 amino acids in length.

3. A cDNA molecule comprising the exons of the nucleic acid molecule of claim 2.

4. The nucleic acid molecule of claim 2, wherein said open reading frame encodes amino acid sequence I.D. No. 2.

5. The nucleic acid molecule of claim 4, which comprises an open reading frame of Sequence I.D. No. 1.

6. A recombinant DNA molecule, comprising a vector having an insert that includes the nucleic acid molecule of claim 1.

7. The recombinant DNA molecule of claim 6, which is cosmid C38, ATCC Accession No. 207208.

8. An isolated nucleic acid molecule which is a gene, having a sequence selected from the group consisting of:

a) An open reading frame defined by exons of Sequence I.D. No. 1;

b) a sequence hybridizing with one or more exons of Sequence I.D. No. 1 or its complement, under conditions calculated to achieve hybridization between sequences according to a formula of: $T_m = 81.5°C. + 16.6 \text{Log}[Na+] + 0.41(\% \ G+C) - 0.63 \ (\% \text{ formamide}) - 600/\#bp$ in duplex;

c) a sequence encoding a polypeptide having Sequence I.D. No. 2; and d) a sequence encoding a polypeptide encoded by a gene contained in cosmid clone C38, designated ATCC Accession No. 207208.

9. A transgenic organism comprising the nucleic acid molecule of claim 1.

10. The transgenic organism of claim 9, which is a plant.

* * * * *